United States Patent
Amzaleg et al.

(10) Patent No.: US 9,235,885 B2
(45) Date of Patent: Jan. 12, 2016

(54) SYSTEM, A METHOD AND A COMPUTER PROGRAM PRODUCT FOR PATCH-BASED DEFECT DETECTION

(71) Applicant: Applied Materials Israel Ltd., Rehovot (IL)

(72) Inventors: Moshe Amzaleg, Beer Sheva (IL); Nir Ben David Dodzin, Hod Hasharon (IL); Vered Gatt, Rehovot (IL); Yair Hanani, Tel Aviv (IL); Efrat Rozenman, Aseret (IL)

(73) Assignee: Applied Materials Israel Ltd, Rehovot (IL)

( * ) Notice: Subject to any disclaimer, the term of this patent is extended or adjusted under 35 U.S.C. 154(b) by 176 days.

(21) Appl. No.: 13/756,399

(22) Filed: Jan. 31, 2013

(65) Prior Publication Data
US 2014/0212021 A1 Jul. 31, 2014

(51) Int. Cl.
G06T 7/00 (2006.01)
G01N 21/956 (2006.01)
H01L 21/66 (2006.01)

(52) U.S. Cl.
CPC .......... G06T 7/001 (2013.01); *G01N 21/95607* (2013.01); *G01N 2021/95615* (2013.01); *G06T 2207/10061* (2013.01); *G06T 2207/30148* (2013.01); *H01L 22/12* (2013.01)

(58) Field of Classification Search
None
See application file for complete search history.

(56) References Cited

U.S. PATENT DOCUMENTS

| | | | | |
|---|---|---|---|---|
| 5,659,172 A * | 8/1997 | Wagner et al. | | 250/307 |
| 5,699,447 A * | 12/1997 | Alumot et al. | | 382/145 |
| 5,982,921 A | 11/1999 | Alumot et al. | | |
| 6,016,357 A * | 1/2000 | Neary et al. | | 382/144 |
| 6,064,484 A * | 5/2000 | Kobayashi et al. | | 356/390 |
| 6,076,465 A * | 6/2000 | Vacca et al. | | 101/481 |
| 6,178,257 B1 | 1/2001 | Alumot et al. | | |
| 6,381,358 B1 * | 4/2002 | Vacca et al. | | 382/145 |
| 6,650,439 B1 * | 11/2003 | Nagarajan et al. | | 358/2.1 |
| 6,829,047 B2 * | 12/2004 | Fujii et al. | | 356/237.4 |
| 6,829,381 B2 * | 12/2004 | Levin et al. | | 382/149 |
| 6,862,491 B2 * | 3/2005 | Levin et al. | | 700/121 |
| 6,952,491 B2 * | 10/2005 | Alumot et al. | | 382/149 |
| 7,054,480 B2 * | 5/2006 | Levin et al. | | 382/154 |
| 7,215,808 B2 * | 5/2007 | Miller | | 382/145 |
| 7,254,263 B2 * | 8/2007 | Ine | | 382/145 |

(Continued)

OTHER PUBLICATIONS

Deshpande et al. "Analytics for building Defect Density Maps" (2011) pp. 1-7.*

*Primary Examiner* — Chan Park
*Assistant Examiner* — Mia M Thomas
(74) *Attorney, Agent, or Firm* — Lowenstein Sandler LLP

(57) ABSTRACT

A system capable of inspecting an article for defects, the system including: a patch comparator, configured to determine with respect to each of a plurality of reference patches in a reference image a similarity level, based on a predefined patch-similarity criterion and on a source patch defined in the reference image; an evaluation module, configured to rate each inspected pixel out of multiple inspected pixels of the inspection image with a representative score which is based on the similarity level of a reference patch associated with a reference pixel corresponding to the inspected pixel; a selection module, configured to select multiple selected inspected pixels based on the representative scores of the multiple inspected pixels; and a defect detection module, configured to determine a presence of a defect in the candidate pixel based on an inspected value of the candidate pixel and inspected values of the selected inspected pixels.

17 Claims, 12 Drawing Sheets

(56) References Cited

U.S. PATENT DOCUMENTS

| | | | |
|---|---|---|---|
| 7,266,232 B2* | 9/2007 | Asai et al. | 382/141 |
| 7,379,580 B2* | 5/2008 | Levin et al. | 382/149 |
| 7,410,737 B2 | 8/2008 | Levin et al. | |
| 7,499,583 B2 | 3/2009 | Alumot et al. | |
| 7,558,419 B1* | 7/2009 | Ye et al. | 382/144 |
| 7,570,796 B2* | 8/2009 | Zafar et al. | 382/144 |
| 7,630,535 B2* | 12/2009 | Isomura | 382/144 |
| 7,676,077 B2* | 3/2010 | Kulkarni et al. | 382/144 |
| 7,796,807 B2 | 9/2010 | Alumot et al. | |
| 7,801,353 B2* | 9/2010 | Almogy et al. | 382/141 |
| 8,041,103 B2* | 10/2011 | Kulkarni et al. | 382/144 |
| 2002/0126888 A1* | 9/2002 | Vacca et al. | 382/145 |
| 2002/0181756 A1* | 12/2002 | Shibuya et al. | 382/145 |
| 2003/0138138 A1* | 7/2003 | Vacca et al. | 382/145 |
| 2003/0223631 A1* | 12/2003 | Ine | 382/145 |
| 2004/0096094 A1* | 5/2004 | Vacca et al. | 382/141 |
| 2007/0081154 A1* | 4/2007 | Mapoles et al. | 356/237.5 |
| 2007/0230770 A1* | 10/2007 | Kulkarni et al. | 382/149 |
| 2008/0106740 A1* | 5/2008 | Yu | 356/434 |
| 2008/0167829 A1* | 7/2008 | Park et al. | 702/81 |
| 2008/0208828 A1* | 8/2008 | Boiman et al. | 707/4 |
| 2008/0250384 A1* | 10/2008 | Duffy et al. | 716/21 |
| 2008/0259328 A1* | 10/2008 | Hirano et al. | 356/237.6 |
| 2009/0080759 A1* | 3/2009 | Bhaskar et al. | 382/141 |
| 2009/0148033 A1* | 6/2009 | Alumot et al. | 382/149 |
| 2009/0257645 A1* | 10/2009 | Chen et al. | 382/145 |
| 2010/0104173 A1* | 4/2010 | Yoshida et al. | 382/145 |
| 2010/0119144 A1* | 5/2010 | Kulkarni et al. | 382/149 |
| 2010/0182602 A1* | 7/2010 | Urano et al. | 356/369 |
| 2011/0013824 A1* | 1/2011 | Yamada | 382/149 |
| 2013/0236084 A1* | 9/2013 | Li et al. | 382/144 |
| 2013/0336573 A1* | 12/2013 | Dalla-Torre et al. | 382/145 |
| 2014/0105482 A1* | 4/2014 | Wu et al. | 382/149 |
| 2014/0307947 A1* | 10/2014 | Kurada et al. | 382/149 |

\* cited by examiner

502 Obtaining the inspection image

504 Generating the inspection image by collecting signals arriving from the article 506 Obtaining the inspection image via a data link interface 508 Obtaining the reference image 530 Defining the reference patches 540 Determining a similarity level with respect to each of a plurality of reference patches included in the reference image 541 Comparing the color values of the pixels in the source patch to the color values of the respective pixels of the relevant reference patch 542 Determining the similarity level with respect to each of the plurality of reference patches based on the results of a comparison between the color values of the pixels of the source patches and those of the pixels of the respective reference patch, and on a predefined patch-similarity criterion which pertains to such a comparison.

570 Determining a presence of a defect in the candidate pixel based on an inspected value of the candidate pixel and inspected values of the selected inspected pixels 571 determining a threshold based on the inspected values of the selected inspected pixels 572 determining of the presence of the defect based on the inspected value of the candidate pixel and on the threshold which is determined based on inspected values of the selected inspected pixels

FIG. 5

```
┌─────────────────────────────────────────────────────────────────────┐
│       810  Obtaining a candidate pixel of the inspection image      │
└─────────────────────────────────────────────────────────────────────┘
                                  │
┌─────────────────────────────────────────────────────────────────────┐
│  820  Defining in each out of multiple reference images multiple source patches │
│  of different shapes, wherein each of the multiple source patches is associated │
│  with the reference source pixel of the respective reference image              │
└─────────────────────────────────────────────────────────────────────┘
                                  │
┌─────────────────────────────────────────────────────────────────────┐
│  830 Defining in each of the reference images multiple reference patches for each │
│  of the source patches of that reference image                       │
└─────────────────────────────────────────────────────────────────────┘
                                  │
┌─────────────────────────────────────────────────────────────────────┐
│  840 In each of the reference images: for each of the multiple source patches, │
│  determining based on that source patch and on a respective patch-similarity   │
│  criterion (i.e. respective to the source patch), multiple similarity levels. Each of │
│  these similarity levels is defined with respect to one of a respective plurality of │
│  reference patches (which are related to one source patch), which is associated │
│  with a reference image pixel                                        │
└─────────────────────────────────────────────────────────────────────┘
                                  │
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│  845 Computing with respect to each inspected pixel out of the multiple │
│  inspected pixels multiple intermediate scores, each of which is     │
│  computed based on the plurality of similarity levels determined for a │
│  corresponding reference image pixel of one of the reference images  │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                                  │
┌─────────────────────────────────────────────────────────────────────┐
│  850 rating each out of the multiple inspected pixels with a representative score │
│  which is based on the plurality of similarity levels determined with respect to │
│  multiple reference patches associated with each out of a plurality of pixels of the │
│  multiple reference images which corresponds to that inspected pixel │
└─────────────────────────────────────────────────────────────────────┘
                                  │
┌─────────────────────────────────────────────────────────────────────┐
│  860  Selecting in the inspection image multiple inspected pixel based on the │
│  representative scores of the multiple inspected pixels              │
└─────────────────────────────────────────────────────────────────────┘
                                  │
┌─────────────────────────────────────────────────────────────────────┐
│  870  Determining a presence of a defect in the candidate pixel based on an │
│  inspected value of the candidate pixel and inspected values of the selected │
│  inspected pixels                                                    │
└─────────────────────────────────────────────────────────────────────┘
                                  │
┌─────────────────────────────────────────────────────────────────────┐
│  880  Providing defect detection results which are based on a result of the │
│  determination of stage 770                                          │
└─────────────────────────────────────────────────────────────────────┘
                                  │
┌─────────────────────────────────────────────────────────────────────┐
│  890  Selectively applying one or more industrial processes in response to a result │
│  of the determination of the presence of the defect                  │
└─────────────────────────────────────────────────────────────────────┘
```

800           FIG. 10

SYSTEM, A METHOD AND A COMPUTER PROGRAM PRODUCT FOR PATCH-BASED DEFECT DETECTION

FIELD

This invention relates to systems, methods and computer program products for patch-based defect detection.

BACKGROUND

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

A conventional in-process monitoring technique employs a two phase "inspection and review" procedure. During the first phase the surface of the wafer is inspected at high-speed and relatively low-resolution. The purpose of the first phase is to produce a defect map showing suspected locations on the wafer having a high probability of a defect. During the second phase the suspected locations are more thoroughly analyzed. Both phases may be implemented by the same device, but this is not necessary.

The two phase inspection tool may have a single detector or multiple detectors. Multiple detector two phase inspection devices are described, by way of example, in U.S. Pat. Nos. 5,699,447, 5,982,921, and 6,178,257.

U.S. patent application Ser. No. 13/495,824 entitled "Apparatus and Method for Defect Detection Including Patch to Patch Comparison" discloses apparatus and method for defect detection including patch to patch comparison.

Defect detection systems for detecting defects in patterned microscopic objects, include for example the following:

United States Patent Application No. USSN 20080106740, entitled "Dual stage defect region identification and defect detection method and apparatus";

United States Patent Application No. USSN 20090148033, "Optical Inspection Apparatus For Substrate Defect Detection";

U.S. Pat. No. 6,064,484, entitled "Pattern inspection method and system";

U.S. Pat. No. 6,829,047, entitled "Defect detection system"; U.S. Pat. No. 7,630,535 entitled "Die-to-die photomask defect detection using region data to modify inspection thresholds";

U.S. Pat. No. 7,801,353, entitled "Method for defect detection using computer aided design data".

State of the art Applied Materials inspection systems are described and claimed in U.S. Pat. Nos. 5,982,921; 6,178,257; 6,952,491; 7,796,807; 7,499,583; 5,699,447; 6,829,381; 7,379,580; 7,410,737; 7,054,480; 6,862,491.

FIG. 1 is an illustration of a wafer 10 such as ones which may be used in the fabrication of integrated circuits and other microdevices. While the term wafer may be used to refer only to the substrate material on which the integrated circuit is fabricated (e.g. a thin slice of semiconductor material, such as a silicon crystal), this term may also be used to refer to the entire construction, including the electronic circuit fabricated on the wafer.

The wafer 10 is divided into multiple dies 11 which are illustrated in a widely implemented rectangular form. Like the term 'wafer', the term 'die' may also be used either for small blocks of semiconducting material, on which a given functional circuit is fabricated, or for such a block including the fabricated electric circuit. Usually, wafer 10 may be cut ("diced") into its multiple dies 11, wherein all of the dies of the wafer contain a copy of the same electronic circuit. While not necessarily so, each of the dies 11 is independently functional.

A single die may include a large amount of patterns that well exceed millions of patterns per die. A semiconductor die usually includes a plurality of layers. A pattern, such as local pattern 24 may be a part of a metal interconnection line, a trench, a via, a conductive gate, etc. Different areas on each die may be put to different uses; such areas may be for example background areas (that are ideally very smooth), memory areas (that include a large number of repetitive patterns) and logic areas (that usually do not include large quantities of adjacent repetitive patterns).

There exists a need for improved and more robust techniques for detecting defects in a substrate, and especially semiconductor substrate defects.

SUMMARY

In accordance with an aspect of the presently disclosed subject matter, there is provided a computerized method for inspecting an article for defects based on processing of inspection images generated by collecting signals arriving from the article, the method including:

obtaining a candidate pixel of the inspection image, the candidate pixel being representative of a candidate article defect location;

in a reference image, defining a source patch associated with a reference source pixel of the reference image which corresponds to the candidate pixel;

in the reference image, based on the source patch and a predefined patch-similarity criterion, determining a similarity level with respect to each of a plurality of reference patches, each of which is associated with a reference image pixel;

in the inspection image, rating each inspected pixel out of multiple inspected pixels with a representative score which is based on the similarity level of a reference patch associated with a reference pixel corresponding to the inspected pixel;

in the inspection image, selecting multiple selected inspected pixels based on the representative scores of the multiple inspected pixels; and determining a presence of a defect in the candidate pixel based on an inspected value of the candidate pixel and inspected values of the selected inspected pixels.

In accordance with an embodiment of the presently disclosed subject matter, there is further provided a method, wherein the defining of the source patch includes defining the source patch so that a size of a smallest rectangle in which all pixels of the source patch are enclosed is smaller than 0.05 times a size of the inspection image.

In accordance with an embodiment of the presently disclosed subject matter, there is yet further provided a method, wherein the determining of the presence of the defect is based on a grey level value of the candidate pixel and on a threshold determined based on grey level values of the selected inspected pixels.

In accordance with an embodiment of the presently disclosed subject matter, the method may also include:

defining in the reference image multiple source patches of different shapes, wherein each of the multiple source patches is associated with the reference source pixel; and for each of the multiple source patches, based on that source patch and a respective patch-similarity criterion, determining a similarity level with respect to each of a respective plurality of reference patches, each of which is associated with a reference image pixel; thereby for each of a plurality of reference image pixels, determining a plurality of similarity levels that are determined for multiple reference patches, of different shapes, which are associated with the respective reference image pixel;

wherein the rating includes rating each inspected pixel out of a subgroup of the multiple inspected pixels with a representative score which is based on the plurality of similarity levels of the multiple reference patches which are associated with a reference pixel corresponding to the inspected pixel.

In accordance with an aspect of the presently disclosed subject matter, there is yet further provided a method, further including: based on a second source patch defined in a second reference image, determining a similarity level with respect to each of a plurality of reference patches, each of which is associated with a pixel of the second reference image; wherein at least one of the representative scores with which one of the multiple inspected pixels is rated is based also on a similarity level of a reference patch associated with a reference pixel of the second reference image which corresponds to the inspected pixel.

In accordance with an embodiment of the presently disclosed subject matter, there is yet further provided a method, wherein the at least one representative score is determined based on a group of similarity levels of reference patches from multiple reference images, so that the score indicates a low degree of similarity between an environment of the inspected pixel and an environment of the candidate pixel if any of the respective similarity levels indicates a low degree of similarity.

In accordance with an embodiment of the presently disclosed subject matter, there is yet further provided a method, further including:

in each image out a plurality of images which includes the reference image: (a) defining multiple source patches of different shapes, wherein each of the multiple source patches is associated with a reference source pixel of the image; and (b) for each of the source patches of the image: based on the source patch and a respective patch-similarity criterion, determining a similarity level with respect to each of a plurality of reference patches, each of which is associated with a pixel of the image; thereby for each of a plurality of pixels of the image, determining a plurality of similarity levels that are determined for multiple reference patches of different shapes which are associated with the respective pixel of the image;

wherein the rating includes rating each inspected pixel out of at least one of the multiple inspected pixels with a representative score which is based on multiple similarity levels of reference patches associated with pixels of the plurality of images which correspond to the inspected pixel.

In accordance with an aspect of the presently disclosed subject matter, there is provided a computerized method for inspecting an article for defects based on processing of inspection images generated by collecting signals arriving from the article, the method including:

obtaining a candidate pixel of the inspection image, the candidate pixel being representative of a candidate article defect location;

in a reference image, defining multiple source patches of different shapes, wherein each of the multiple source patches is associated with a reference source pixel of the reference image which corresponds to the candidate pixel;

in the reference image, for each of the multiple source patches, based on that source patch and a respective patch-similarity criterion, determining a similarity level with respect to each of a respective plurality of reference patches, each of which is associated with a reference image pixel; thereby for each of a plurality of reference image pixels, determining a plurality of similarity levels that are determined for multiple reference patches, of different shapes, which are associated with the respective reference image pixel;

in the inspection image, rating each inspected pixel out of multiple inspected pixels with a representative score which is based on the similarity level of a reference patch associated with a reference pixel corresponding to the inspected pixel; wherein the rating includes rating each inspected pixel out of a subgroup of the multiple inspected pixels with a representative score which is based on the plurality of similarity levels of the multiple reference patches which are associated with a reference pixel corresponding to the inspected pixel;

in the inspection image, selecting multiple selected inspected pixels based on the representative scores of the multiple inspected pixels; and determining a presence of a defect in the candidate pixel based on an inspected value of the candidate pixel and inspected values of the selected inspected pixels.

In accordance with an aspect of the presently disclosed subject matter, there is provided a computerized method for inspecting an article for defects based on processing of inspection images generated by collecting signals arriving from the article, the method including:

obtaining a candidate pixel of the inspection image, the candidate pixel being representative of a candidate article defect location;

in each image out a plurality of images which includes a reference image: (a) defining multiple source patches of different shapes, wherein each of the multiple source patches is associated with a reference source pixel of the image; and (b) for each of the source patches of the image: based on the source patch and a respective patch-similarity criterion, determining a similarity level with respect to each of a plurality of reference patches, each of which is associated with a pixel of the image; thereby for each of a plurality of pixels of the image, determining a plurality of similarity levels that are determined for multiple reference patches of different shapes which are associated with the respective pixel of the image;

in the inspection image, rating each inspected pixel out of multiple inspected pixels with a representative score which is based on the similarity level of a reference patch associated with a reference pixel corresponding to the inspected pixel; wherein the rating includes rating each inspected pixel out of at least one of the multiple inspected pixels with a representative score which is based on multiple similarity levels of reference patches associated with pixels of the plurality of images which correspond to the inspected pixel.

in the inspection image, selecting multiple selected inspected pixels based on the representative scores of the multiple inspected pixels; and determining a presence of a defect in the candidate pixel based on an inspected value of the candidate pixel and inspected values of the selected inspected pixels.

In accordance with an aspect of the presently disclosed subject matter, there is yet further provided a system capable of inspecting an article for defects, the system including:

a patch comparator, configured to determine with respect to each of a plurality of reference patches in a reference image a similarity level, based on a predefined patch-similarity criterion and on a source patch which is defined in the reference image and which is associated with a reference source pixel of the reference image; wherein the reference source pixel corresponds to a candidate pixel of an inspection image that is generated by collecting signals arriving from the article, the candidate pixel being representative of a candidate article defect location; wherein each of the plurality of reference patches is associated with a reference image pixel;

an evaluation module, configured to rate each inspected pixel out of multiple inspected pixels of the inspection image with a representative score which is based on the similarity level of a reference patch associated with a reference pixel corresponding to the inspected pixel;

a selection module, configured to select multiple selected inspected pixels based on the representative scores of the multiple inspected pixels; and a defect detection module, configured to determine a presence of a defect in the candidate pixel based on an inspected value of the candidate pixel and inspected values of the selected inspected pixels.

In accordance with an embodiment of the presently disclosed subject matter, there is yet further provided a system 8, wherein a size of a smallest rectangle in which all pixels of the source patch are enclosed is smaller than 0.05 times a size of the inspection image.

In accordance with an embodiment of the presently disclosed subject matter, there is yet further provided a system, wherein the defect detection module is configured to determine the presence of the defect based on a grey level value of the candidate pixel and on a threshold determined based on grey level values of the selected inspected pixels.

In accordance with an embodiment of the presently disclosed subject matter, there is yet further provided a system, wherein multiple source patches of different shapes are defined in the reference image, each of the multiple source patches is associated with the reference source pixel; wherein the patch comparator is configured to determine for each of the multiple source patches, based on that source patch and a respective patch-similarity criterion, a similarity level with respect to each of a respective plurality of reference patches, each of which is associated with a reference image pixel; thereby for each of a plurality of reference image pixels, determining a plurality of similarity levels that are determined for multiple reference patches of different shapes which are associated with the respective reference image pixel; wherein the elevation module is configured to rate each inspected pixel out of a subgroup of the multiple inspected pixels with a representative score which is based on the plurality of similarity levels of the multiple reference patches which are associated with a reference pixel corresponding to the inspected pixel.

In accordance with an embodiment of the presently disclosed subject matter, there is yet further provided a system, wherein the patch comparator is further configured to determine, based on a second source patch defined in a second reference image, a similarity level with respect to each of a plurality of reference patches, each of which is associated with a pixel of the second reference image; wherein the evaluation module is configured to determine at least one of the representative scores with which one of the multiple inspected pixels is rated based also on a similarity level of a reference patch associated with a reference pixel of the second reference image which corresponds to the inspected pixel.

In accordance with an embodiment of the presently disclosed subject matter, there is yet further provided a system, wherein the evaluation module is configured to determine the at least one representative score based on a group of similarity levels of reference patches from multiple reference images, so that the score indicates a low degree of similarity between an environment of the inspected pixel and an environment of the candidate pixel if any of the respective similarity levels indicates a low degree of similarity.

In accordance with an embodiment of the presently disclosed subject matter, there is yet further provided a system, wherein in each image out a plurality of images which includes the reference image multiple source patches of different shapes are defined, each of the multiple source patches is associated with a reference source pixel of the image; wherein the patch comparator is configured to determine in each image of the plurality of images, for each of the source patches of the image a similarity level with respect to each of a plurality of reference patches based on the source patch and a respective patch-similarity criterion, wherein each of the plurality of reference patches is associated with a pixel of the image; thereby for each of a plurality of pixels of the image, determining a plurality of similarity levels that are determined for multiple reference patches of different shapes which are associated with the respective pixel of the image; wherein the evaluation module is configured to rate each inspected pixel out of at least one of the multiple inspected pixels with a representative score which is based on multiple similarity levels of reference patches associated with pixels of the plurality of images which correspond to the inspected pixel.

In accordance with an aspect of the presently disclosed subject matter, there is yet further provided a program storage device readable by machine, tangibly embodying a program of instructions executable by the machine to perform method for inspecting an article for defects based on processing of inspection images generated by collecting signals arriving from the article, including the steps of:

obtaining a candidate pixel of the inspection image, the candidate pixel being representative of a candidate article defect location;

in a reference image, defining a source patch associated with a reference source pixel of the reference image which corresponds to the candidate pixel;

in the reference image, based on the source patch and a predefined patch-similarity criterion, determining a similarity level with respect to each of a plurality of reference patches, each of which is associated with a reference image pixel;

in the inspection image, rating each inspected pixel out of multiple inspected pixels with a representative score which is based on the similarity level of a reference patch associated with a reference pixel corresponding to the inspected pixel;

in the inspection image, selecting multiple selected inspected pixels based on the representative scores of the multiple inspected pixels; and determining a presence of a defect in the candidate pixel based on an inspected value of the candidate pixel and inspected values of the selected inspected pixels.

Optionally, the defining of the source patch includes defining the source patch so that a size of a smallest rectangle in which all pixels of the source patch are enclosed is smaller than 0.05 times a size of the inspection image.

Optionally the determining of the presence of the defect is based on a grey level value of the candidate pixel and on a threshold determined based on grey level values of the selected inspected pixels.

Optionally, the program of instructions further include instructions executable by the machine for: (a) defining in the reference image multiple source patches of different shapes, wherein each of the multiple source patches is associated with the reference source pixel; and (b) for each of the multiple source patches, based on that source patch and a respective patch-similarity criterion, determining a similarity level with respect to each of a respective plurality of reference patches, each of which is associated with a reference image pixel; thereby for each of a plurality of reference image pixels, determining a plurality of similarity levels that are determined for multiple reference patches, of different shapes, which are associated with the respective reference image pixel; wherein the rating includes rating each inspected pixel out of a subgroup of the multiple inspected pixels with a representative score which is based on the plurality of similarity levels of the multiple reference patches which are associated with a reference pixel corresponding to the inspected pixel.

Optionally, the program of instructions further include instructions executable by the machine for: based on a second source patch defined in a second reference image (and optionally also on a second patch-similarity criterion), determining a similarity level with respect to each of a plurality of reference patches, each of which is associated with a pixel of the second reference image; wherein at least one of the representative scores with which one of the multiple inspected pixels is rated is based also on a similarity level of a reference patch associated with a reference pixel of the second reference image which corresponds to the inspected pixel.

Optionally, the at least one representative score is determined based on a group of similarity levels of reference patches from multiple reference images, so that the score indicates a low degree of similarity between an environment of the inspected pixel and an environment of the candidate pixel if any of the respective similarity levels indicates a low degree of similarity.

Optionally, the program of instructions further include instructions executable by the machine for: in each image out a plurality of images which includes the reference image: (a) defining multiple source patches of different shapes, wherein each of the multiple source patches is associated with a reference source pixel of the image; and (b) for each of the source patches of the image: based on the source patch and a respective patch-similarity criterion, determining a similarity level with respect to each of a plurality of reference patches, each of which is associated with a pixel of the image; thereby for each of a plurality of pixels of the image, determining a plurality of similarity levels that are determined for multiple reference patches of different shapes which are associated with the respective pixel of the image; wherein the rating includes rating each inspected pixel out of at least one of the multiple inspected pixels with a representative score which is based on multiple similarity levels of reference patches associated with pixels of the plurality of images which correspond to the inspected pixel.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 5 illustrates optional stages of the method of FIG. 3, according to various embodiments of the invention;

FIG. 10 is a flowchart of a computerized method for inspecting an article for defects based on processing of inspection images generated by collecting signals arriving from the article, according to an embodiment of the invention;

Figure 1:
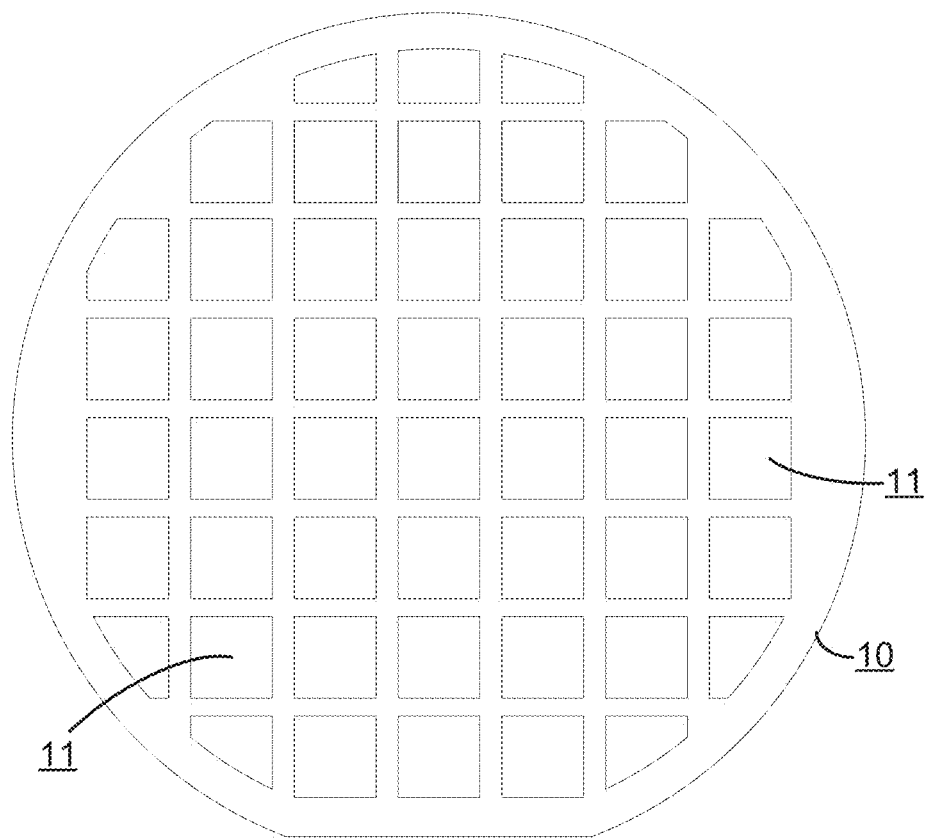
FIG. 1 is an illustration of a wafer such as ones which may be used in the fabrication of integrated circuits and other microdevices.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "calculating", "determining", "generating", "setting", "configuring", "selecting", "defining", "computing" or the like, include action and/or processes of a computer that manipulate and/or transform data into other data, said data represented as physical quantities, e.g. such as electronic quantities, and/or said data representing the physical objects. The terms "computer", "processor", "controller", and "processing module" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

Figure 2:
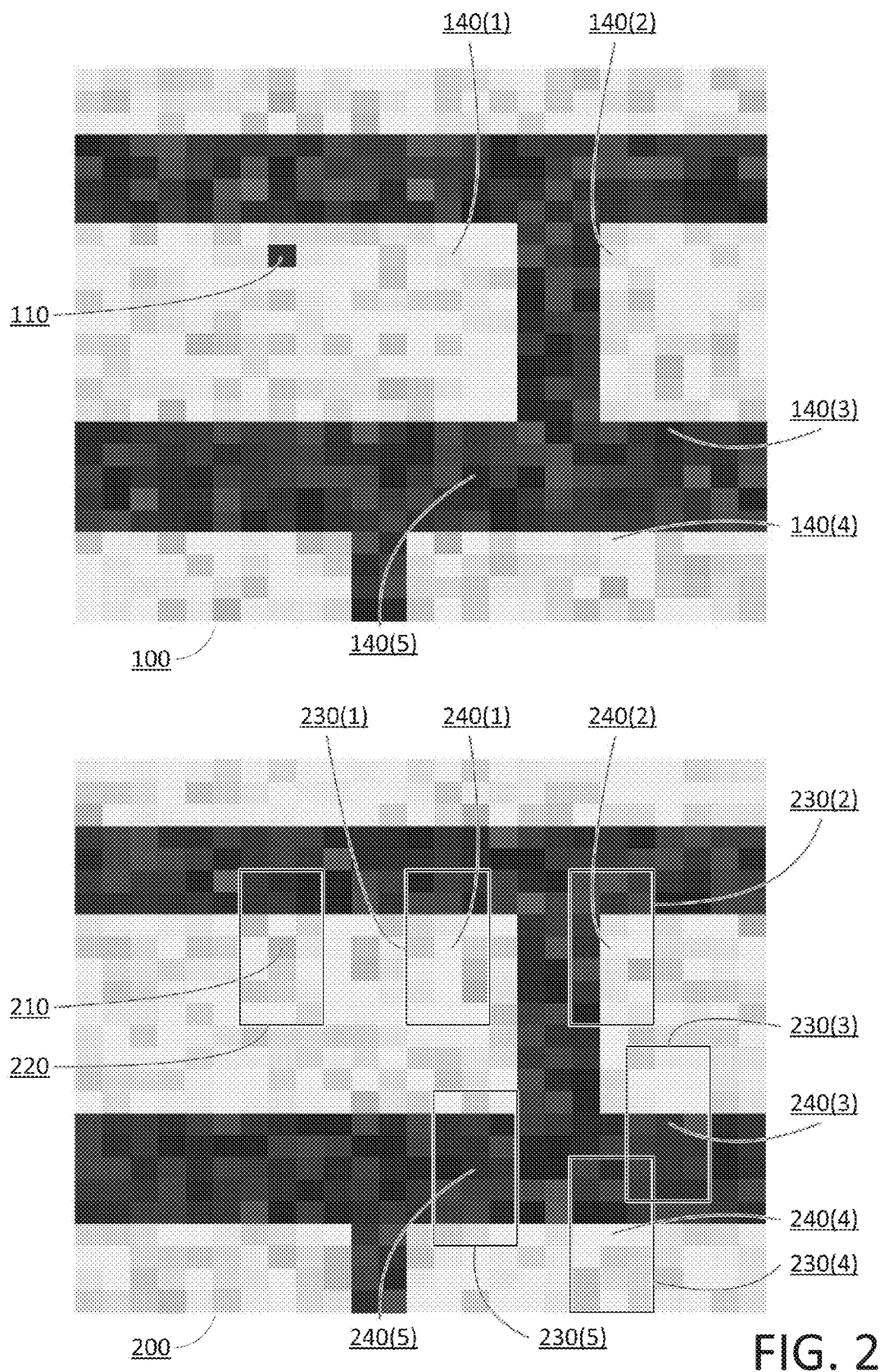
FIG. 2 illustrates an inspection image and a reference image, according to an embodiment of the invention.

FIG. 2 illustrates inspection image 100 and a reference image 200, according to an embodiment of the invention. Inspection image 100 is generated by collecting signals arriving from an article, such as a wafer, an electronic circuit, a photomask used for the manufacturing of wafers, and so on. It is noted that reference image 200 may also generated by collecting signals arriving from an article—either the same article or another one. For example, inspection image 100 may be generated by collecting signals arriving from a first die of a given wafer, and reference image 200 may be generated by collecting signals arriving from another die of the same wafer. It should be noted that while images 100 and 200 are exemplified as 25 by 25 pixels images, in practical implementations the images are usually significantly larger, by several orders of magnitude.

Inspection image 100 includes a pixel denoted as "candidate pixel 110". Candidate pixel 110 may be selected in different ways. For example, candidate pixel 110 may be representative of a candidate article defect location, which is determined by a process of defect detection (which may include, for example, comparing inspection image 100 and reference image 200, or another reference image). However, the candidate pixel may be selected otherwise. For example, the candidate pixel may be selected according to a selection order, according to which pixels of the reference image are selected, irrespective of any other image (e.g. any pixel of the inspection image may serve as a candidate pixel in its turn). It is noted that the candidate article defect may be larger than one pixel. In such a case, a decision rule may be used to select the candidate pixel to represent the candidate article defect (e.g. the pixel nearer the center, the pixel most different than a reference pixel of a reference image, based on design data, e.g. computer assisted design data—"CAD", etc.).

It is noted that the term "pixel" is very well known in the art and should be construed in a non-limiting way as including (though not necessarily limited to) an element of an image which has a color value (e.g. a gray level value), and a defined location within the image (e.g. integer x and y coordinates). The location of the pixel with respect to the image of which it is a part is relative to a location of the article imaged in the respective image.

The term "defect" is also very well known in the art, and should be construed in a non-limiting way as including (though not necessarily limited to) an undesirable local change that may kill the chip or affect its reliability.

It is noted that any of images 100 and 200 may be a part of a larger image (e.g. a selected area out of a larger image). The way in which the area denoted as image 100 (or 200) may be selected out of a larger image does not affect the employment of the following processes and systems, and is therefore not elaborated.

For simplicity of explanation it will be assumed that inspection image 100 and reference image 200 are substantially similar. Such similarity may be achieved by collecting signals from substantially similar areas of the article. For example, the positioning of an area of a wafer which is covered by inspection image 100 with respect to a first die (or cell, in a cell-to-cell comparison scheme) in which it is included may be substantially the same as the positioning of an area of the wafer which is covered by reference image 200 with respect to a second die (cell) in which it is included.

For the sake of simplicity it is assumed that inspection image 100 and reference image 200 are aligned to each other and that for each pixel of the inspection image, it is assumed that there is exactly one pixel of the reference image which corresponds to it. That is, it is assumed that for each pixel (i, j) of the inspection image, there is a pixel (i+n, j+m) which corresponds to it (wherein n and m are constant integers). It is noted that if the reference image does not fulfill this condition, it may be processed to provide an image that does fulfill that condition.

Corresponding pixels of different images are assumed to represent corresponding locations of the article (or corresponding locations in similar articles). For example, assuming that a pixel P(insp) of the inspection image and pixel P(ref) of the reference image are corresponding to each other, the positioning of an area of the wafer which is represented by pixel P(insp) with respect to the first die (or cell) in which that area is included may be substantially the same as the positioning of an area of the wafer which is represented by pixel P(ref) with respect to the second die (cell) in which it is included.

Each pixel in any of the images has an inspected value which is representative of that pixel. The inspected value may be simply a color-value of the respective pixel, or a color-based attribute which is based on the color-value, but this is not necessarily so. In a gray-level (GL) image, the inspected value may be the one-dimensional color value of the respective pixel. In a color image, the inspected value may be a one-dimensional color value in one out of multiple color channels (e.g. Red, Green, or Blue, in an RGB image), an intensity value, a color identifier, and so on. While in some implementations the inspected value may be representative of other pixels apart from the selected pixel (e.g. an average of the color of the selected pixels and of its 8 immediately adjacent pixels), in other implementations the inspected value is representative only of the selected pixel and is irrespective of information of other pixels (such as neighboring pixels).

Referring to candidate pixel 110, reference image 200 includes a reference source pixel 210, which corresponds to the candidate pixel 100. The additional pixels and areas illustrated in FIG. 2 are discussed below, as they are defined or utilized in the course of method 500.

Figure 3:
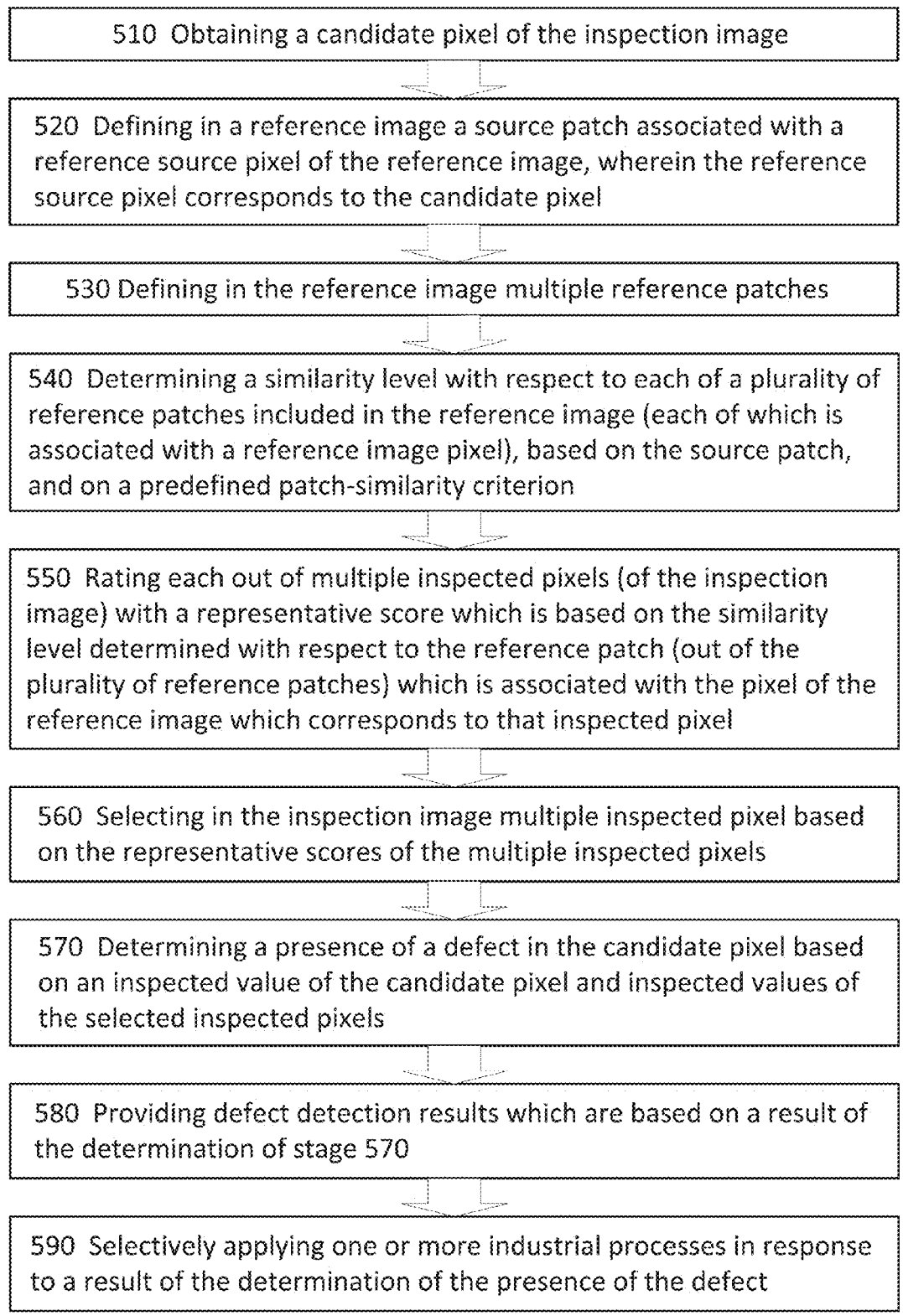
FIG. 3 is a flowchart of a computerized method for inspecting an article for defects based on processing of inspection images generated by collecting signals arriving from the article, according to an embodiment of the invention.

FIG. 3 is a flowchart of computerized method 500 for inspecting an article for defects based on processing of inspection images generated by collecting signals arriving from the article, according to an embodiment of the invention. Referring to the examples set forth in other drawings, method 500 may be carried out by system 200. Different embodiments of system 200 may implement the various disclosed variations of method 500 even if not explicitly elaborated. Likewise, different embodiments of method 500 may include stages whose execution fulfills the various disclosed variations of system 200, even if succinctness and clarity of description did not necessitate such repetition.

Method 500 may be implemented for various types of articles, from a very minute scale (e.g. millimetric or nanoscale objects) to larger objects such as a geographical area imaged from an airplane or from a satellite. In order to clarify the disclosure, different stages of method 500 would be exemplified using an example of an article which is selected from a group consisting of an electronic circuit, a wafer, and a photomask (a partially transparent plate which may be used for the manufacturing of electronic circuits or other objects in a process implementing transmitting light through such a photomask, such as photolithography).

It is noted that while method 500 is described as a method for inspecting an article for defects (or at least potential defects), a person who is of ordinary skill in the art would understand that method 500 may equivalently be implemented for detection of many other types of items within various types of articles. For example, apart from deviations from an expected pattern (such as a hole in a textile fabric, or a potential manufacturing defect in a wafer), other kinds of items which may be identified are specific items or a group thereof (e.g. looking for tanks in aerial images or for intruders in security camera data).

Stage 510 of method 500 includes obtaining a candidate pixel of the inspection image. Optionally, the candidate pixel may be representative of a candidate article defect location. Referring to the examples set forth with respect to the following drawings, stage 510 may be carried out by a processing module such as modules 920, 930.

The obtaining of the candidate pixel includes information regarding the candidate pixel and/or information by which the candidate pixel may be identified. For example, the obtaining may include a location of the candidate pixel (e.g. X, Y coordinate thereof with respect to the inspection image). Additional information which may be obtained regarding the candidate pixel may include, for example, one or more of the following: color information of the pixel, a population and/or classification of pixels to which the pixel belong (e.g. noise based population), and so on.

It is noted that the obtaining of stage 510 may be implemented in different ways in different embodiments of the invention. For example, the obtaining may include obtaining only information of the candidate pixel, but may also include obtaining information of additional pixels of the inspection image. Furthermore, the obtaining may include obtaining the information of the candidate pixel from an external system (e.g. from an external inspection unit, external camera or detector, and so on), and/or obtaining such information by capturing (or otherwise generating) the aforementioned pixel information, or the larger part of the inspection image. Method 500 may include a stage of capturing the image information (e.g. as part of a scanning of the inspected object). Various possible implementations of the capturing of the pixel information are discussed with respect to optional stage 502, which is illustrated in FIG. 5.

It is noted that stage 510 may include acquiring a list of at least one candidate pixel of the inspection image. The list may include, for example, a list of potential defects found by a previous classification system. It is noted that while not necessarily so, the method may include analyzing parts or all of the inspection images for selecting the one or more candidate pixels based on results of the analysis. Also, the method may further include selecting a proper subset of the candidate pixels, and excluding others from the selection. For example, if the list of candidate pixels (e.g. the list of potential defects) identifies several adjacent pixels, stage 510 may include selecting a representative candidate pixel out of a group of adjacent pixels (e.g. based on defect likelihood score given in a preceding classification stage).

Stage 520 of method 500 includes defining in a reference image a source patch associated with a reference source pixel of the reference image, wherein the reference source pixel corresponds to the candidate pixel. Referring to the examples set forth with respect to the previous drawings, the reference image may be reference image 200, with the possible variations and various implementations discussed above. Likewise, the reference source pixel is exemplified by reference source pixel 210, and the source patch is exemplified by source patch 220.

The defining of the source patch may include selecting the reference source pixel within the reference image (e.g. based on the location of the candidate pixel with respect to the inspection image), and defining the source patch based on the selected reference source pixel and a patch-shape. Such a patch-shape may be a predefined patch-shape, a patch-shape selected out of a plurality of predefined patch-shapes, or defined based on an analysis of the inspection image and/or one or more reference images. Referring to the examples set forth with respect to the following drawings, stage 520 may be carried out by a processing module such as patch comparator 930.

Figure 4:
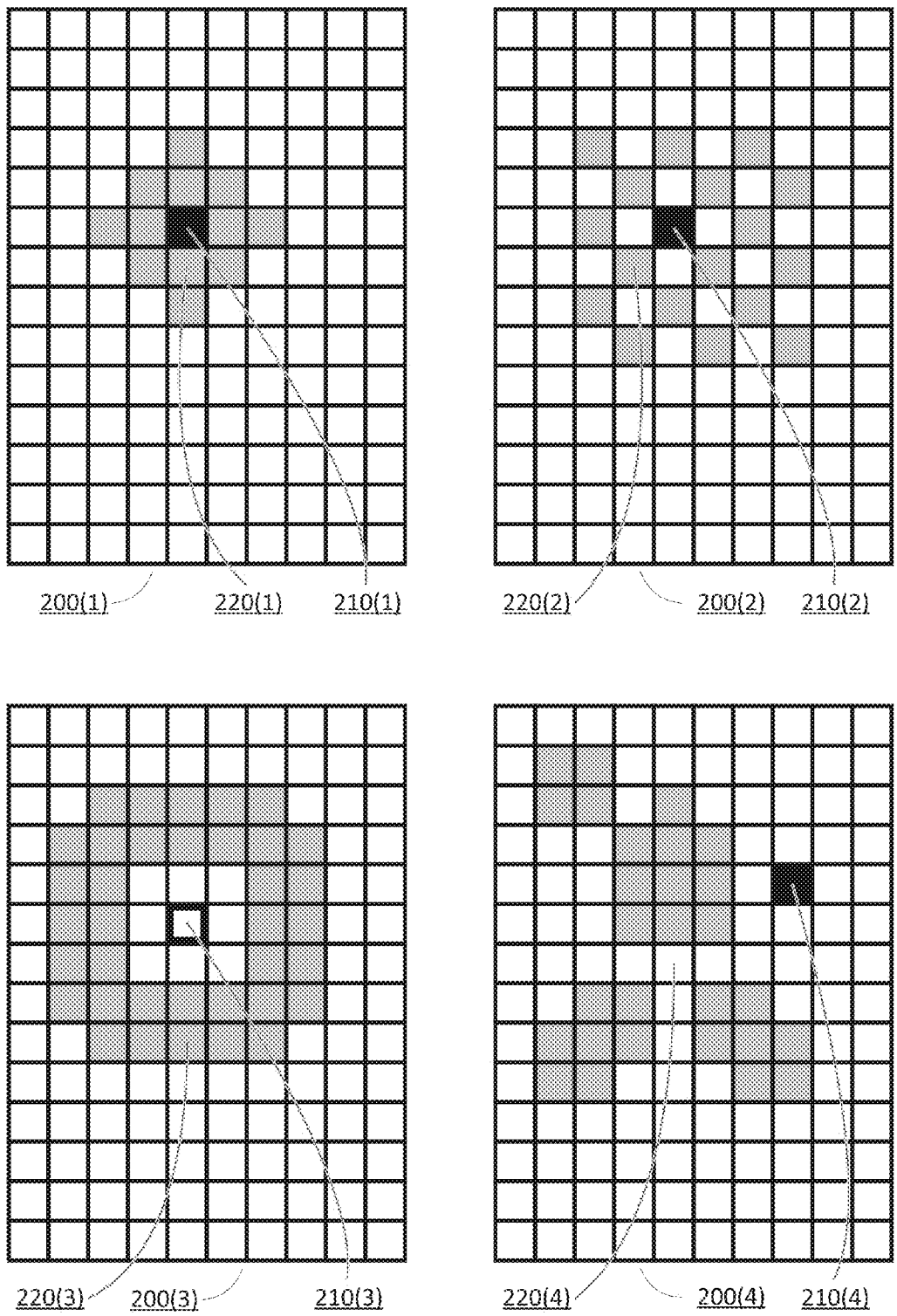
FIG. 4 illustrates various possible patches, according to various embodiments of the invention.

FIG. 4 illustrates various possible patches, according to various embodiments of the invention. The illustrated patches are source patches, but reference patches may be of similar shapes. A patch (also referred to as "kernel") is in essence, in the context of the present document, a group of pixels. The pixels which form a patch are arranged in a given shape with respect to the correlative pixel (and are thereby associated therewith). Provided a given patch-shape a patch is associated with a given pixel of the reference image if it includes pixels which are arranged in that patch-shape with respect to that given pixel.

By way of example, if the patch-shape is symmetrical (like the rectangular patch illustrated in FIG. 2, or patches 220(1) and 220(3) of FIG. 4), then the given pixel to which the patch is associated may be located in the center of the patch shape (as exemplified in the aforementioned illustrations). However, the pixel to which the patch is associated (given a known patch-shape) is not necessarily positioned in a center of the patch-shape (e.g. as exemplified in patch 220(2)) or even inside it (e.g. as exemplified in patch 220(4)). Furthermore, such a pixel may possibly not form a part of the patch which is associated thereto (e.g. as exemplified in patch 220(3)). The pixels forming the patch may be adjacent to one another, but this is not necessarily so, and in some implementations isolated pixels or isolated groups of pixels (e.g. as exemplified in patch 220(4)) may be part of the patch.

It is noted that while not necessarily so, patches may be relatively small with respect to the image. Firstly, the number of the pixels included in any of the patches of method 500 may be smaller than 100, and optionally even smaller—e.g. smaller than 30 (as in the illustrated examples of patches, except for patch 220(3)). Especially, optionally, the defining of stage 220 includes defining a source patch which includes less than 100 pixels. Optionally, the defining of stage 220 includes defining a source patch which includes less than 40 pixels. Selecting patches which include relatively few pixels have some advantages in at least some of the possible implementations of method 500, as will be clear after method 500 is discussed, and as is further elaborated below.

Not only may the number of pixels be relatively small, the size of the patches may be quite limited as well. That is, the pixels forming each of the patches may be proximate to one another, and to the pixel to which the respective patch is associated (e.g. the distance between any of the pixels in a patch to the pixel to which the respective patch is associated may be smaller than 20 pixels, either directly or diagonally). Naturally, the degree of proximity may depend on the implementation (e.g. the type and size of the inspected article, the type and size of potential defect, the inspection resolution, and so on).

The relatively small size of the patches may be defined with respect to the image in which each of the patches is included. For example, optionally the defining of some or all of the patches during method 500 (and especially the defining of the source patch) may include defining the respective patch so that a size of a smallest rectangle in which all pixels of the respective patch (e.g. the source patch) are enclosed is smaller than 0.05 times a size of the image in which the patch is included (e.g. the reference image in which the source patch is included).

The size of the source patch may be a predetermined size (even though it may optionally be determined on a per-pixel basis, or on another varying basis). The actual size selected for the source patch may depend on various factors such as the inspection device and its characteristic errors, the subject matter of the image and its characteristics, the available computation power, the characteristics of potential defects, and so on.

Using small patches allows comparing each source patch to many other patches of the reference image, thereby providing a large population for statistical analysis (e.g. as discussed below).

Reverting to FIG. 3, stage 540 of method 500 includes determining a similarity level with respect to each of a plurality of reference patches included in the reference image (each of which is associated with a reference image pixel), wherein the determining includes determining the similarity level for each of the plurality of the reference patches based on the source patch, and on a predefined patch-similarity criterion. Referring to the examples set forth with respect to the following drawings, stage 540 may be carried out by a processing module such as patch comparator 930.

In other words, stage 540 includes: in the reference image, based on the source patch and the predefined patch-similarity criterion, determining a similarity level with respect to each of the plurality of reference patches, each of which is associated with a respective reference image pixel.

It should be noted that even if the inspection image and the reference image are aligned to one another, alignment errors would always occur. Notably, stage 540 does not include comparing between a patch of the inspection image to a patch of the reference image—a comparison which is susceptible to such errors—but rather includes determining similarity levels based on patches of a single image—the respective reference image.

While different types of similarity levels may be utilized in different implementations of the invention, the patch-similarity criterion used for the determining of these levels is defined so that reference patches which resemble the source patch in at least one criterion are assigned a similarity level indicating a greater degree of similarity than reference patches which do not resemble the source patch. Some such patch-similarity criterions are offered below as examples, but other criterions may be devised to suit different implementations.

The aspect of similarity which the patch-similarity criterion should emphasize depends on the desired implementations. For example, considering a wafer inspection implementation, it may be desirable to find areas of the wafer which are in similar distance from a similarly-size conductor as the candidate article defect location.

Referring to the examples set forth with respect to FIG. 2, it is noted that some reference patches 230 are illustrated, each of which is associated with a reference image pixel denoted 240 (that is, reference patch 230(*i*) is associated with reference image pixel 240(*i*), for i=1 . . . 5). As can be seen, optionally, the reference patches may be of the same patch-shape as the source patch (e.g. as exemplified in FIG. 2), but this is not necessarily so.

It is noted that the determining of stage 540 may be preceded by stage 530 of defining the reference patches. Such defining of the reference pixels may include defining of the patch-shape of the reference patches (if not necessarily identical to that of the source patch), selecting of a plurality of reference image pixels (with which the reference patches are to be associated), and based on this information defining the reference patches. Referring to the examples set forth with respect to the previous drawings, stage 530 may be carried out by a processing module such as patch comparator 930.

The selecting of the plurality of reference image pixels (or more directly, the defining of the reference pixels) may include selecting all reference image pixels (or reference patches) which may be defined in the reference image (or an area of which), but this is not necessarily so. For example, given the 25 by 25 pixels reference image 200 and 3 by 7 pixels reference patches 230 exemplified in FIG. 2, a total of 23×19 (=437) pixels may be utilized to defined reference patches associated therewith (thereby possibly defining 437 reference patches). However, fewer reference patches may be defined. For example, out of these possible 437 pixels, every other pixel may be selected. The selection may also be based on an analysis of the inspection image and/or one or more reference images.

Reverting to stage 540, in which a similarity level (also referred to as "provisional score") is determined with respect to each of the plurality of reference patches which are included in the reference image. It is noted that while the similarity level is determined with respect to a patch, it may also be considered to be determined with respect to a pixel (e.g. the reference image pixel with which the respective reference patch is associated). The storing of the similarity levels determined in stage 540 may be done on a pixel basis. That is, an image may be generated so that the color value (e.g. gray level value—GL) of each pixel of the new image is the similarity level determined to a corresponding pixel of the reference image.

As aforementioned, the determining includes determining the similarity level for each of the plurality of the reference patches based on the source patch, and on a predefined patch-similarity criterion.

Optionally, the patch-similarity criterion may pertain to pixel-to-pixel comparisons of the color value of the pixels of the source patch to those of the relevant reference patch.

Stage 540 may include stage 541 of comparing the color values (e.g. GL values) of the pixels in the source patch to the color values of the respective pixels of the relevant reference patch (e.g. by subtracting the GL value of each pixel of the source patch from the GL value of the correspondingly located pixel of the reference patch).

Stage 540 may include stage 542 of determining the similarity level with respect to each of the plurality of reference patches based on the results of a comparison between the color values of the pixels of the source patches and those of the pixels of the respective reference patch, and on a predefined patch-similarity criterion which pertains to such a comparison.

In just a few examples, if the comparing process for a source patch (e.g. 3×7 pixels sized, pertaining to the example of FIG. 2) and a similar sized reference patch yielded N difference values (e.g. GL difference values), stage 542 may include selecting as the similarity level of that reference patch one of the following values:

The maximum absolute value difference value out of the N values;

The minimum absolute value difference value out of the N values;

An average of all N difference values;

The second maximal difference value out of the N values;

Mean of top 10 difference values out of the N values, and so on and so forth.

It is noted that a numerically higher similarity level may be given to patches of relatively high similarity but also to such of relatively low similarity, depending on the specific implementations. For example, selecting the maximum absolute value of difference value out of the N values, for example, would give a numerically low similarity level—which in such implementations indicates a high degree of similarity—to a reference patch only if each pixel of the reference patch has a color value which is similar to that of the respective pixel of the source patch.

Referring to the example of FIG. 2, according to such a patch-similarity criterion, reference patch 230(1) (which has top two dark rows and five lower rows—like source patch 220) would be assigned a relatively low numeric similarity level—which in such an implementation indicates a high degree of similarity. In such an implementation, however, reference patches 240(2), 240(3), 240(4) and 240(5) would all receive a similar similarity level indicating a low degree of similarity (each having at least one dark pixel which corresponds to a bright pixel of the source patch and vice versa)—and no significant differentiation of similarity level is achieved. This is therefore a relatively strict patch similarity criterion.

In comparison, selecting the average of all N difference values would still result in reference patch 230(1) being assigned a relatively low numeric similarity level (indicating, as before, a high degree of similarity). However, greater differentiation is achieved between the other reference patches: the similarity level assigned to reference patch 230(4) (whose dark third row corresponds to a row of bright pixels of the source patch) is significantly different than the one assigned to reference patch 240(3) (whose bright third row is the only row similar to the corresponding row of source patch 220). This is therefore a more gradual patch-similarity criterion.

The selection of the patch-similarity criterion may depend on the actual implementation (e.g. based on the strict level required).

As will be discussed below in greater detail, similarity levels may be assigned to more than one set of reference patches, each such set of reference patches including a plurality of reference patches which are compared to a single source patch (out of multiple source patches).

Stage 550 of method 500 includes rating each out of multiple inspected pixels (of the inspection image) with a representative score which is based on the similarity level determined with respect to the reference patch (out of the plurality of reference patches) which is associated with the pixel of the reference image which corresponds to that inspected pixel. Optionally, each pixel of the inspection image for which a corresponding reference pixel of the reference image was assigned a similarity level (in stage 540) may be rated at stage 550. However, this is not necessarily so, and fewer inspected pixels may be rated. Referring to the examples set forth with respect to the following drawings, stage 550 may be carried out by an evaluation module such as evaluation module 940.

In other words, stage 550 includes: in the inspection image, rating each inspected pixel out of multiple inspected pixels with a representative score which is based on the similarity level of a reference patch associated with a reference pixel corresponding to the inspected pixel. It is noted that in some implementations, the representative score with which such an inspected pixel is rated may be based on several similarity levels, each determined with respect to a different reference patch which is associated with a reference image pixel that corresponds to the inspected pixel.

Referring to the example of FIG. 2, several such inspected pixels 140 are illustrated, so that reference image pixel 240(i) of reference image 200 corresponds to inspected pixel 140(i) of inspection image 100, for i=1 . . . 5.

If only a single reference patch is associated with a reference pixel corresponding to each of the multiple inspected pixels, the similarity level determined with respect to that reference patch may be used to determine the representative score (e.g. the same score may be used).

However, as will be discussed below, in some implementations of the invention, more than one reference patch is associated with one or more reference pixels (of one or more reference images) which corresponds to some or all of the inspected pixels. In such cases (which are discussed below in greater detail), the rating may be based on multiple such similarity levels.

While not necessarily so, additional parameters may also be used in the rating (for example, CAD data may be used to determine areas of a wafer which are more susceptible to errors and are therefore less desirable for comparison).

The representative score is assigned to a pixel of the inspection image based (at least) on the similarity level determined with respect to the reference patch associated with the corresponding pixel of the reference image. The similarity level, in turn, is indicative of a similarity between a reference patch (the source patch) and a patch which is associated with that corresponding pixel. Therefore, the representative score is also indicative of similarity. It should be noted that the aforementioned similarity of which the representative score is indicative is not similarity between pixels, areas or patches of the inspection image, but rather similarity between patches of the reference image. In some implementations, the representative score may be computed also based on similarity indicative factors which pertain to pixels, areas or patches of the inspection image, but in some implementations it is irrespective thereof.

Stage 560 of method 500 includes selecting in the inspection image multiple inspected pixels (referred to as "selected inspected pixels") based on the representative scores of the multiple inspected pixels. Referring to the examples set forth with respect to the following drawings, stage 560 may be carried out by a selection module such as selection module

950. In other words, stage 560 includes: in the inspection image, selecting multiple selected inspected pixels based on the representative scores of the multiple inspected pixels.

Different selection rules may be used for the selecting of the selected inspected pixels out of the multiple inspected pixels. For example, each inspected pixel rated with a representative score which is higher (alternatively: lower) than a threshold may be selected (the threshold may be predetermined or computed as part of stage 560). In another example, the M inspected pixels with the highest (alternatively: lowest) representative score may be selected (M being a predetermined positive integer). That is, optionally, the selecting of stage 560 may include selecting in the inspection image a predetermined number of inspected pixels. The M pixels selected as selected inspected pixels may be those whose similarity levels indicate that their environment most resemble that of the candidate pixel.

It is noted that a combination of these two approaches may also be used, by selecting a number of selected inspected image which is between M1 and M2 (for example, M1>10 and M2/M1<1.5).

While not necessarily so, additional parameters may also be used in the selecting of stage 560 (for example, CAD data may be used to determine areas of a wafer which are more susceptible to errors and are therefore less desirable for comparison).

As discussed below, the selected inspected pixels are utilized in stage 570 for determining a presence of a defect in the candidate pixel. The group of selected pixels may be considered as a comparison group of pixels to which the candidate pixel may be compared for determining the presence of the defect. Taking stages 520 through 560 as a whole, it is noted that this group of pixels is selected based (at least partly, optionally primarily, and possibly exclusively) on a criterion of similarity between patches (the aforementioned patch-similarity criterion).

It should however be noted that even though the candidate pixel which is representative of a candidate article defect location belongs to the inspection image, the patch-similarity criterion is not applied to patches in the inspection image, but rather to reference image patches. This is true even (as is the usual case) in implementations in which the candidate article defect location is not represented by any pixel of the reference image.

The reference source pixel is assumed to represent a location of an article which corresponds to that represented by the candidate pixel (as aforementioned, corresponding pixels of different image are assumed to represent corresponding locations of the article, or corresponding locations in similar articles). By extension, the article area which surrounds the location represented by the reference source pixel (hereinafter referred to as the "reference area") is assumed to correspond to the area which surrounds the location represented by the candidate pixel (hereinafter referred to as the "candidate area").

While there is a candidate article defect in the "candidate area" (a candidate defect whose size is not necessarily known, and which may be larger than one pixel), the chances that there is also a defect in the "reference area" are relatively low (assuming that defects are relatively scarce). Therefore, finding areas of the article which are similar to the "reference area" enables finding areas of the article which are similar to a presumably non-defective version of the "candidate area". While these areas are found in an article area represented by the reference image, corresponding areas may be located in the vicinity of the candidate article defect location (i.e. in a part of the article represented by the inspection image). As in the aforementioned example, there is a relatively low chance that these corresponding areas are also defective, and a very low chance that a significant portion of them are defective.

Pixels which represent locations in these presumably non-defective corresponding areas (which resemble the "candidate area") may be selected so that the locations of these pixels correspond to the location of the candidate pixel—and these selected pixels (the selected inspected pixels) may therefore be used as a reference group for the candidate pixels.

Stage 570 of method 500 includes determining a presence of a defect in the candidate pixel based on an inspected value of the candidate pixel and inspected values of the selected inspected pixels (and possibly on other parameters as well, e.g. ones associated with the candidate pixel). Referring to the examples set forth with respect to the following drawings, stage 570 may be carried out by a defect detection module such as defect detection module 960.

Optionally, the determining of the presence of the defect in stage 570 may be based on a grey level value of the candidate pixel and on a threshold determined based on grey level values of the selected inspected pixels. Additional discussion is provided, by way of example, with respect to FIG. 11.

Stage 570 includes classifying the candidate pixel (e.g. as defective or not-defective). A result of stage 570 may be based on the color information (e.g. GL value) and on the color information of the selected inspected pixels, but may also be based on the kernels surrounding those pixels, e.g. similarly to the determining of the similarity between patches in stage 540). In is noted that apart from defectiveness, stage 570 may include classifying the candidate pixel based on another type of a classification system (e.g. a class of pixels which require further processing, a class of pixel by which detection or inspection criteria ought to be modified, etc.).

Optionally, the determining of the presence of the defect may be based on a threshold which is determined based on the inspected values of the selected inspected pixels (denoted stage 571). According to such an embodiment of the invention, the determining of the presence of the defect may be based on the inspected value of the candidate pixel (e.g. the GL value of the candidate pixel) and on the threshold which is determined based on inspected values (e.g. GL values) of the selected inspected pixels (572).

For example, a difference between the inspected value of the candidate pixel and the inspected value of the reference source pixel (which is the pixel of the reference image which corresponds to the candidate pixel) may be determined, and compared to a threshold which is determined based on the inspected values of the selected inspected pixels. If the difference is higher than the threshold, then the determining of stage 570 may conclude with determining that a defect is present in the candidate pixel, and if the difference is lower than that threshold then method 500 may include determining that there is no presence of a defect in the candidate pixel.

Additional variations of ways for determining the presence of a defect in the candidate pixel are discussed with respect to FIGS. 3 through 11.

It is noted that the determining of the presence of a defect in the candidate pixel may be a binary determination (i.e. present or non-present, defective or non-defective, and so on), but this is not necessarily so. Optionally, the determining of the presence of a defect in the candidate pixel may use a defect-indicative classification system which has more than two classes (i.e. more than just the classes of "having a possible defect" and "not having a possible defect").

If the candidate pixel is not defective then resemblance between the candidate pixel and the multiple selected pixels should also be discernible in the inspection image. However, if the candidate pixel is indeed defective (or otherwise different from the corresponding pixels in the reference image), then it may be expected to be substantially different than the selected pixels, selected only based on information of the reference images, but not on information of the inspection image.

Stage 570 may be followed by optional stage 580 of providing defect detection results which are based on a result of the determination of stage 570. The defect detection results may be provided in various ways (e.g. using a display, a communication interface, and so forth), and to one or more targets (e.g. to a human, to another system, and so forth). Referring to the examples set forth with respect to the previous drawings, stage 580 may be carried out by an interface such as output interface 970.

Stage 570 may be followed by a stage of reporting one or more defects, if multiple selected pixels are processed in multiple iterations of the preceding stages (e.g. as part of the results provided in stage 580). The reporting may include reporting location information of at least one of the defects (and possibly of all of them) in pixel coordinates, in coordinates of the inspected object, in coordinates of a corresponding design data, etc.

The results provided may further include additional information identifying one or more defects which were identified within the inspection image, such as one or more of the following (e.g. as a part of a defect list):

Location information of one or more defective pixels);
Size information, indicating size of the defects;
Type information, identifying initial classification of the defect;
Small image excerpts of the inspection image, each of which includes one or more defective pixels;
Grade of the item in one or more grading systems (e.g. indication of the likelihood of defectiveness of the indicated potential defect).

Method 500 may further include optional stage 590 of selectively applying one or more industrial processes in response to a result of the determination of the presence of the defect. Clearly, in different embodiments of the invention, different industrial processes may be applied. For example, stage 590 may include applying any combination of one or more of the following industrial processes:

A production industrial process (e.g. further examining the inspected object, discarding the inspected object and/or another item, selecting a process which the inspected object needs to undergo, etc.);
A chemical industrial process (e.g. applying to the inspected object a chemical material whose concentration is selected and/or manipulated based on the results of stage 570, etc.);
A mechanical industrial process (e.g. applying mechanical force onto the inspected object, etc.);
An information technology industrial process (e.g. writing information to a database and/or tangible storage, modifying communication routing channel, encrypting, etc.);

Method 500 may also continue with other actions that are based on the determined presence of the defect. For example, stage 590 may include selectively scanning areas of the inspected object in a resolution higher than the resolution of the inspection image, based on a result of stage 570. In such a case, the areas selected for further scanning may be selected based on the locations of potential defects which are classified into certain classes but not into at least one of the other classes. Referring to the examples set forth in the previous drawings, such inspection may be carried out by an inspection machine such as inspection machine 910, or by a posterior inspection module (which may be another inspection machine), such as posterior inspection module 980. For example, if the inspected object is indeed a wafer, the inspection image may be obtained using Electron Beam Inspection (EBI) in a first resolution, while the potential defects selected, based on the way in which they were classified, may be further inspected in much higher resolution by a Defect Review Scanning Electron Microscope (DRSEM).

Stage 590 may also include declaring the wafer (or specific dies thereof) as operational or nonoperational based on the results of stage 570 and/or the results of stage 590 (e.g. the high resolution inspection).

Inspecting only potential defects which for which a presence of a defect was determined in stage 570, while not inspecting other potential defects (e.g. received in a preliminary defects lists prior to stage 520) saves time and resources, and may also improve the results of the inspection. For example, scanning less areas of the wafer would lead to less accumulation of electrical charge resulting from the electrons beamed by the electron beam scanning apparatus.

FIG. 5 illustrates optional stages of method 500, according to various embodiments of the invention. The stages which are illustrated in FIG. 5 but not in FIG. 3 are optional, and the different possible combinations of those stages and of stages 510 through 580 (and their optional sub-stages) may be implemented in different embodiments of the invention.

Stage 510 may be preceded by stage 502 obtaining the inspection image. Stage 502 may include stage 506 of obtaining the inspection image via a data link interface. Stage 502 may include stage 504 of generating the inspection image by collecting signals arriving from the article. Stage 504 may include scanning an area of the inspected article (e.g. the wafer) to provide scanned image data.

The scanning of the scanned area may be a part of larger parts of the wafer—e.g. a die, multiple dies, or even the entire wafer (or at least the parts of which that include electronic circuit parts). The scanning may be carried out in different techniques such as electron beam scanning and optical scanning. Referring to the examples set forth in the previous drawings, stage 504 may be carried out by any scanning, imaging and/or detecting apparatus such as inspection machine 910.

An implementation of the scanning of stage 504 for scanning a wafer may include, for example, the following sub-steps: (a) illuminating an inspected die; (b) collecting detection signals arriving from the article by at least one detector; (c) processing the detection signals to provide an image of a portion of the illuminated die, the image including a grid of pixels, each characterized by a signal such as a gray level signal; and optionally (d) selecting which pixel out of the grid of pixels to currently process, said pixel being the selected pixel. The selection may follow a predefined pattern, such as a raster scan pattern, but other selection schemes may be implemented.

Since the scanning may be a lengthy process, some or all of the other stages (e.g. any one or more of stages 510 through 580) may be carried out at least partly concurrently with the scanning of one or more parts of the inspected object, such as the scanning of the scanned area of the inspected object in stage 504. Alternatively, stage 504 may entirely precede stage 510, and possibly other stages of method 500 (e.g. stages 520, 530, 550, 560). The scanned image data (or part thereof) may be processed in order to determine the inspected values of one or more of the pixels (e.g. that of the candidate pixel). The scanned image data and/or the inspected value and the reference value may be stored in a database which is stored in a tangible memory, whether volatile (e.g. DRAM, SRAM) and/or non-volatile (e.g. Hard-drive, Flash memory).

Method 500 may further include additional stages that precede the optional scanning of the scanned area in stage 504, such as wafer alignment and translation of the wafer so that the reference area may be scanned. The global alignment of the wafer (e.g. by aligning a stage on which the wafer is positioned) may be based, for example, on CAD data, using coarse anchor points from the design data. For example, coarse registration on a single large target by the Applied Materials patented RGA algorithm may be implemented. The translation of the wafer may include translating the wafer to a position in which the reference die may be scanned. Alignment methods are known in the art. An illustration of a method for such an alignment is described in U.S. Pat. Nos. 5,699,447, 5,982,921 and 6,178,257B1 of Alumot. Another alignment method is described in U.S. Pat. No. 5,659,172 of Wagner.

The information required for successful execution of such preliminary stages may be retrieved from a previously determined recipe (or recipe parameters) and/or from a configuration file (referred to as "config") which does not pertain to a specific scan or to a specific layer of a wafer, but rather to a configuration of the scanning machine executed right after its manufacture (or at a later time, irrespective of any specific target to be scanned).

Method 500 may also include stage 508 of obtaining the reference image. Stage 508 may be implemented in various manners, such as those discussed with respect to stage 502. For example, stage 508 may include obtaining the reference image via a data link interface. Stage 508 may also include generating the reference image by collecting signals arriving from the article (or from a similar article).

Figure 6:
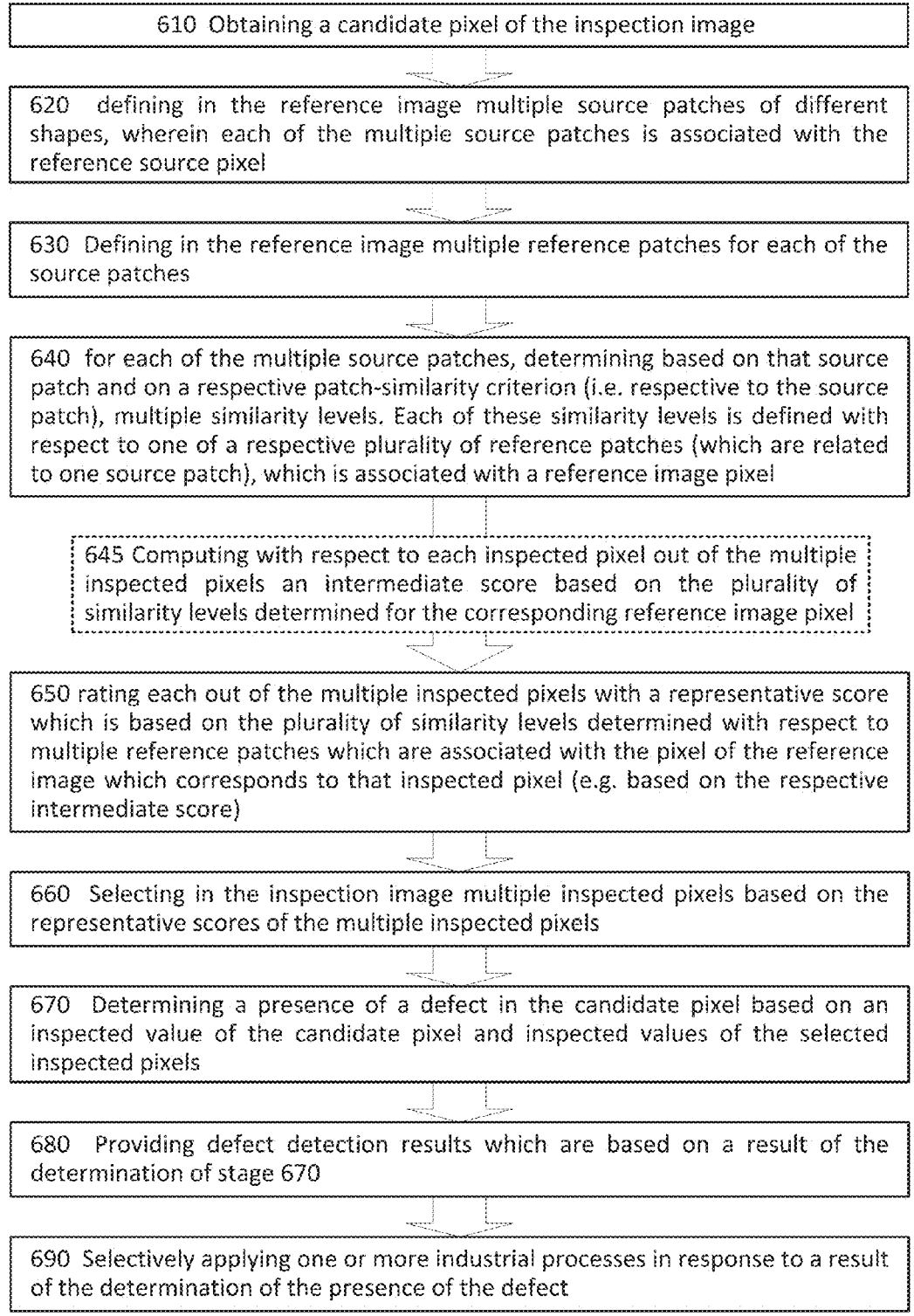
FIG. 6 is a flowchart of a computerized method for inspecting an article for defects based on processing of inspection images generated by collecting signals arriving from the article, according to an embodiment of the invention.

FIG. 6 is a flowchart of computerized method 600 for inspecting an article for defects based on processing of inspection images generated by collecting signals arriving from the article, according to an embodiment of the invention.

Method 600 is a variation of method 500, in which patches of different shapes are implemented in the reference image. The numbering of the stages of method 600 is similar to that of method 500 (e.g. stage 620 is equivalent to stage 520). All variations and possible implementations which are discussed with respect to a given stage of method 500 may be implemented, mutatis mutandis, for the equivalent stage of method 600.

Stage 620 includes defining in the reference image multiple source patches of different shapes, wherein each of the multiple source patches is associated with the reference source pixel (which, as aforementioned, corresponds to the candidate pixel). Referring to the examples set forth with respect to the previous drawings, stage 620 may be carried out by a processing module such as patch comparator 930. Referring to the example of FIG. 4, any two or more of source patches 220(1), 220(2), 220(3), and 220(4) may be defined as source patches. Clearly, the possible shapes of source patches are not restricted to these four shapes. Referring for example to the rectangular source patches exemplified in FIG. 2, it is noted that if a first source patch out of the multiple source patches is a rectangular source patch of a given orientation (e.g. a vertical orientation, as illustrated), another source patch of the multiple source patches may be a rectangular source patch of a different orientation (e.g. horizontal orientation). For example, any subgroup of the following source patches sizes (without giving examples from non-rectangular patch sizes) may be selected: 1×1, 1×5, 5×1, 3×5, 5×3, 3×9, 9×3, 5×7, 7×5, 7×7, 9×9, 12×4, 5×12, and so on.

The selection of source patches of different shapes may be implemented for detecting different aspects of similarity between a surrounding of the reference source pixel to other areas of the reference image (a similarity which may imply a similarity between a surrounding of the candidate pixel to corresponding areas of the inspection image). For example, utilizing rectangular source patches of different orientations may be utilized to detect similarity between such image areas in corresponding orientations (e.g. X axis and Y axis directions). In another example, using source patches (e.g. square, rectangular, circular, etc.) of different sizes (e.g. one confined within the exterior boundaries of the other) may be utilized to detect similarity in near surroundings of the source reference pixel, as well as similarity in an area a bit further from that pixel.

It is noted that optionally, for two (or more) out of the aforementioned multiple source patches, each one of these source patches may include at least one pixel of the reference image which is not included in the other. That is, optionally, a relative complement of a first patch of the multiple source patches in a second patch of the multiple source patches is non-empty, and a relative complement of the second patch in the first patch is likewise non-empty.

Stage 640 includes: for each of the multiple source patches, determining based on that source patch and on a respective patch-similarity criterion (i.e. respective to the source patch), multiple similarity levels. Each of these similarity levels is defined with respect to one of a respective plurality of reference patches (which are related to one source patch), which is associated with a reference image pixel. Execution of stage 640 results in determining for each of a plurality of reference image pixels a respective plurality of similarity levels which are determined for multiple reference patches of different shapes which are associated with the respective reference image pixel.

In other words, stage 640 includes: for each of the multiple source patches, based on that source patch and on a respective patch-similarity criterion, determining a similarity level with respect to each of the respective plurality of reference patches, each of which is associated with a reference image pixel; thereby for each of a plurality of reference image pixels, determining a plurality of similarity levels that are determined for multiple reference patches of different shapes which are associated with the respective reference image pixel. It is noted that different patch-similarity criterions may be utilized for different source patches, but this is not necessarily so.

Figure 7:
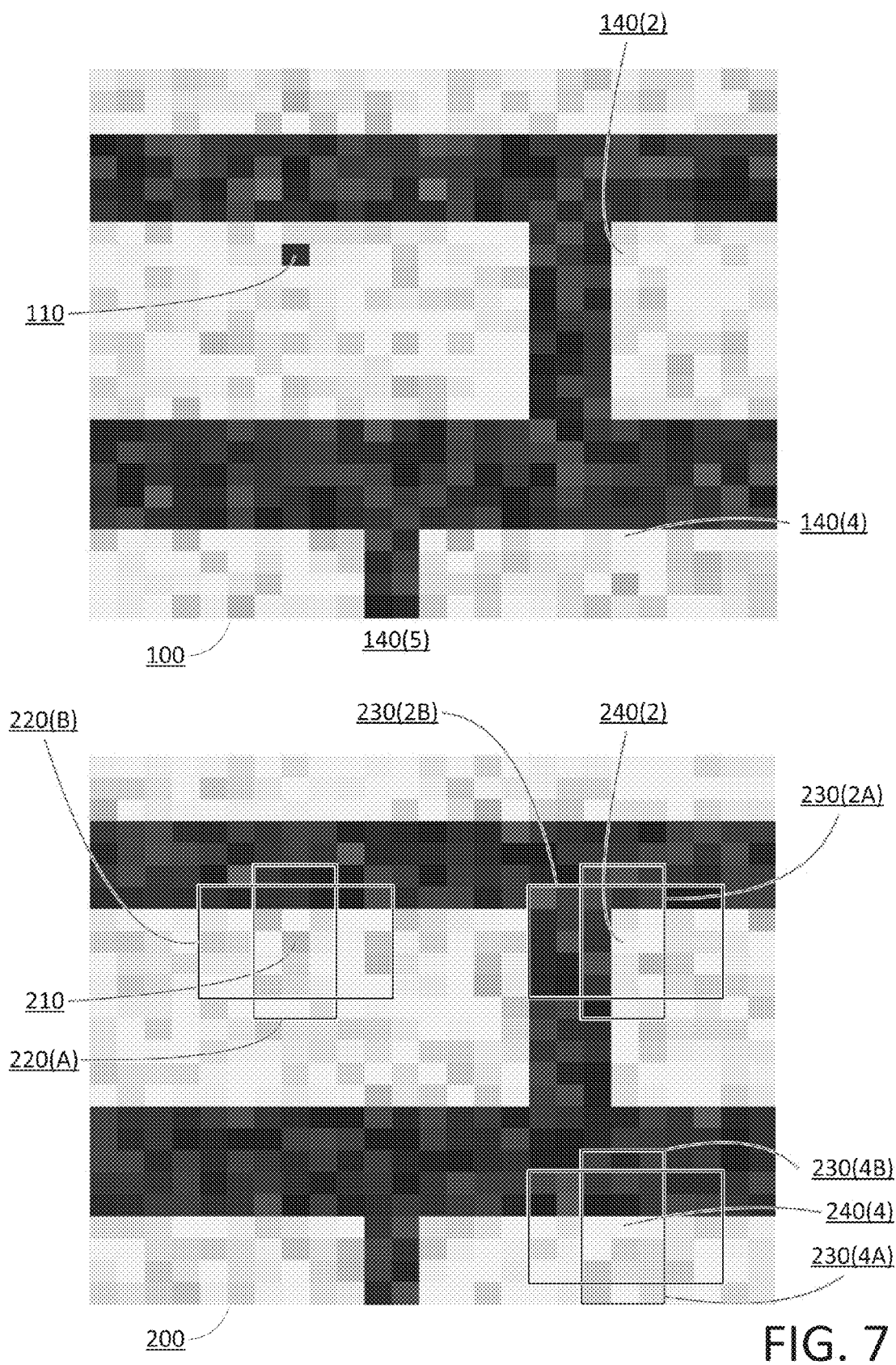
FIG. 7 illustrates various possible patches, according to various embodiments of the invention.

Referring to the example of FIG. 7, two source patches are defined, patch 220(A) and patch 220(B). For each out of a plurality of reference pixels (which in the illustration includes only two pixels 240(2) and 240(4), for reasons of clarity of illustration) two respective patches are defined—patches 230(2A) and 230(2B) for reference pixel 240(2) and patches 230(4A) and 230(4B) for reference pixel 240(4). It is noted that while in the illustrated example the same number of reference patches is associated with each of the plurality of pixels, this is not necessarily so, and different reference pixels may be associated with a different number of patches (this number possibly ranging between 1 and the number of defined source patches). For example, for reference pixels which are near the edge of the reference image, some patches may not be defined while others may possibly be.

Reverting to FIG. 6, it is noted that the determining of stage 640 may be preceded by stage 630 of defining in the reference image multiple reference patches for each of the source patches. Such defining of the reference pixels may include defining of the patch-shape of the reference patches (if not necessarily identical to that of the respective source patch), selecting of a plurality of reference image pixels (with which the reference patches are to be associated), and based on this information, defining the reference patches. Referring to the examples set forth with respect to the previous drawings, stage 630 may be carried out by a processing module such as patch comparator 930.

Stage 650 includes rating each of a subgroup of the multiple inspected pixels with a representative score which is based on the plurality of similarity levels determined for that inspected pixel. Stage 650 includes rating each inspected pixel out of a subgroup of the multiple inspected pixels with a representative score which is based on the plurality of similarity levels of the multiple reference patches which are associated with a reference pixel corresponding to the inspected pixel. That is, stage 650 includes rating each out of the subgroup of the multiple inspected pixels with a representative score which is based on the plurality of similarity levels determined with respect to multiple reference patches which are associated with the pixel of the reference image which corresponds to that inspected pixel. Referring to the examples set forth with respect to the previous drawings, stage 650 may be carried out by an evaluation module such as evaluation module 940. The subgroup may include some or all of the multiple inspected pixels.

The representative scores which are determined in stage 650 may later be used in some or all of stages 660, 670, 680, and 690, which are similar to stages 560, 570, 580, and 590 (respectively). For reasons of brevity of disclosure, the discussion which relates to stages 560, 570, 580, and 590 is not repeated here, because it applies to method 600 as well.

It is therefore clear that stage 660 includes selecting pixels of the inspection image based on multiple representative scores of pixels of the inspection image, and that stage 670 includes determining a presence of a defect in the candidate pixel based on the inspected values of these selected inspected pixels—which as aforementioned where selected based on similarity levels which pertain to source patches of different shapes.

Stage 640 includes determining a plurality of similarity levels (each relating to a reference patch of a different shape) for each out of a plurality of pixels. As aforementioned, utilizing source patches of different shapes may be implemented for detecting different aspects of similarity between image areas. Thus, for each out of this plurality of pixels of the reference image, different similarity levels may be determined, each indicative of degree of similarity with respect to a given similarity aspect (e.g. similarity in the horizontal direction, similarity in the vertical direction, similarity in immediate environment, similarity in a larger environment, and so on).

The rating of the corresponding pixels of the inspection image may account in various ways for such different similarity levels. For example, the rating may be implemented so that a pixel of the inspection image would be rated as similar if its corresponding reference-image pixel was scored as similar in any similarity aspects—even if only one. In other implementations, such a pixel would not be rated as similar if its corresponding pixel in the reference image was not scored as similar in at least N>1 similar aspects, and possibly in all of them. These two alternatives are merely examples, and clearly significantly more complex rules may also be implemented.

For example, method 600 may include computing a score (also referred to in the following paragraph as "the computed score") with respect to each inspected pixel out of the multiple inspected pixels (or of another group of inspection image pixels which shares at least one pixel with the group of multiple inspected pixels). The computed score is computed with respect to each of these pixels based on the plurality of similarity levels determined for the corresponding reference image pixel (i.e. similarity levels determined with respect to reference patches of different shapes which are associated to the pixels in the reference image which corresponds to the pixel for which the score is computed). The resulting computed score may be saved to a tangible storage in a memory entry associated with the respective pixel of the inspection image, and/or with the corresponding pixel of the reference image. As will be further discussed later, the selecting of stage 660 may be based on these computed scores (if such computation is implemented).

Such a score may be computed in different ways. For example, the score computed with respect to each of the pixel may be computed based on the aforementioned multiple similarity levels so that this score indicates a high degree of similarity between an environment of the inspected pixel and an environment of the candidate pixel if any of the respective similarity levels indicates a high degree of similarity.

It is noted that the computing of such scores (also referred to in the several previous paragraphs as the "computed scores") may be implemented as part of the rating of stage 650. Even more so, the representative scores computed in stage 650 (or at least some of them) may be such computed scores. For example, stage 650 may include rating each out of one or more of the multiple inspected pixels with the representative score which is based on the plurality of similarity levels determined with respect to multiple reference patches which are associated with the pixel of the reference image which corresponds to that inspected pixel, so that this representative score indicates a high degree of similarity between an environment of the inspected pixel and an environment of the candidate pixel if any of the respective similarity levels indicates a high degree of similarity.

Alternatively, the computed score which is computed with respect to a given inspected pixel may be computed before the representative score associated with that pixel, wherein the determining of that representative score is based on the computed score (in such a case also referred to as "intermediate score"), and possibly on additional parameters (e.g. as discussed with respect to method 800).

That is, optionally, method 600 may include stage 645 of computing with respect to each inspected pixel out of the multiple inspected pixels (or of another group as discussed above) an intermediate score, based on the plurality of similarity levels determined for the corresponding reference image pixel. Stage 645 may be implemented in different ways. For example, stage 645 may include computing the intermediate score based on the aforementioned multiple similarity levels so that this intermediate score indicates a high degree of similarity between an environment of the inspected pixel and an environment of the candidate pixel if any of the respective similarity levels indicates a high degree of similarity.

Computing an intermediate score based on similarity levels of patches of different shapes from the same image may be used, for example, if implementing patches in multiple reference images. In such a case, intermediate scores computed with respect to an inspection image pixel may be the basis for the rating of such a pixel with a matching representative score.

Figure 8:
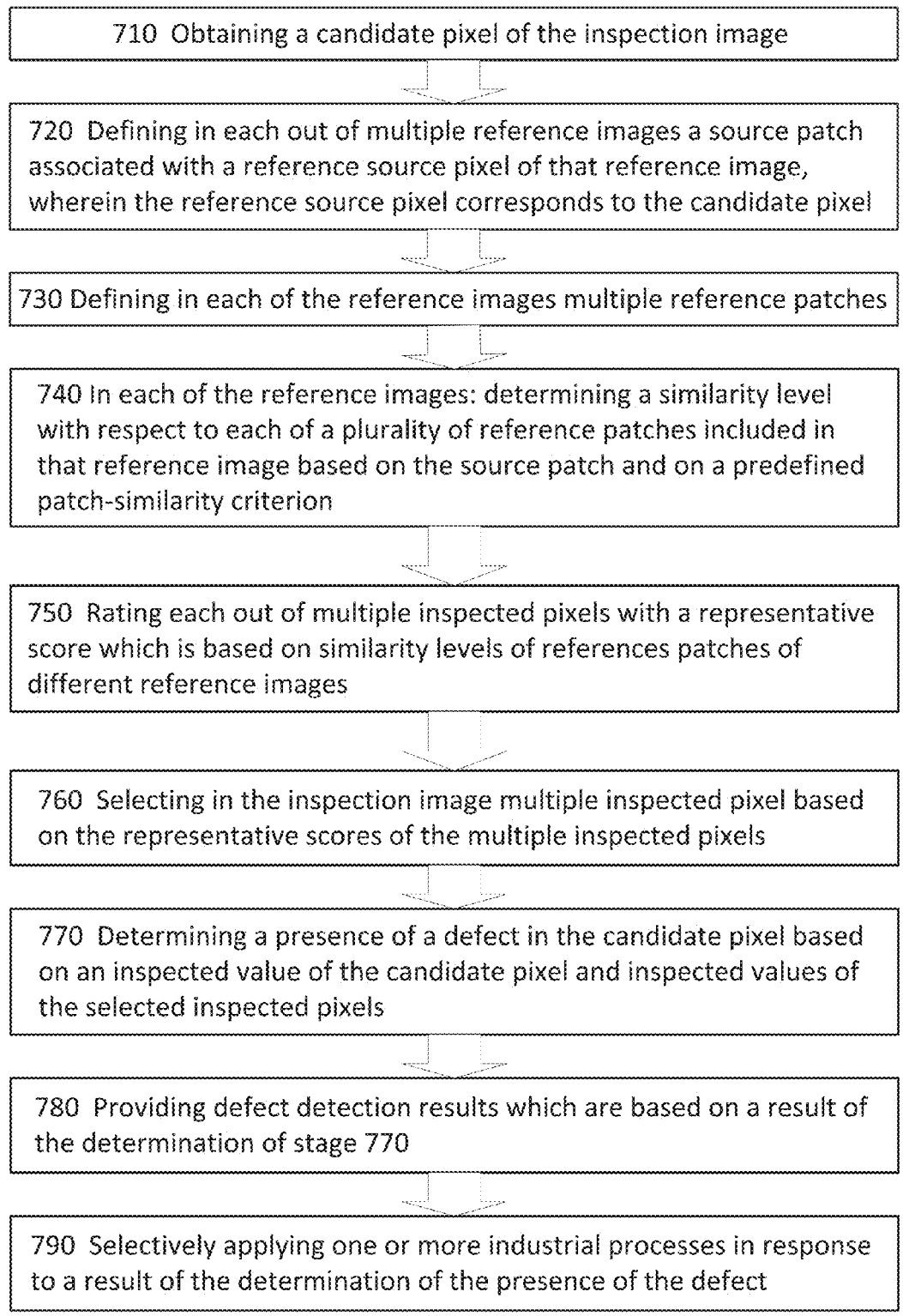
FIG. 8 is a flowchart of a computerized method for inspecting an article for defects based on processing of inspection images generated by collecting signals arriving from the article, according to an embodiment of the invention.

FIG. 8 is a flowchart of computerized method 700 for inspecting an article for defects based on processing of inspection images generated by collecting signals arriving from the article, according to an embodiment of the invention.

Method 700 is a variation of method 500, in which patches are defined and used in multiple reference images. The numbering of the stages of method 700 is similar to that of method 500 (e.g. stage 720 is equivalent to stage 520). All variations and possible implementations which are discussed with respect to a given stage of method 500 may be implemented, mutatis mutandis, for the equivalent stage of method 700.

In essence, stages 520 and 540 (and also 530, if implemented) are repeated for multiple different reference images, and the rating of stage 750 is based on similarity levels determined with respect to patches of different reference images.

Figure 9:
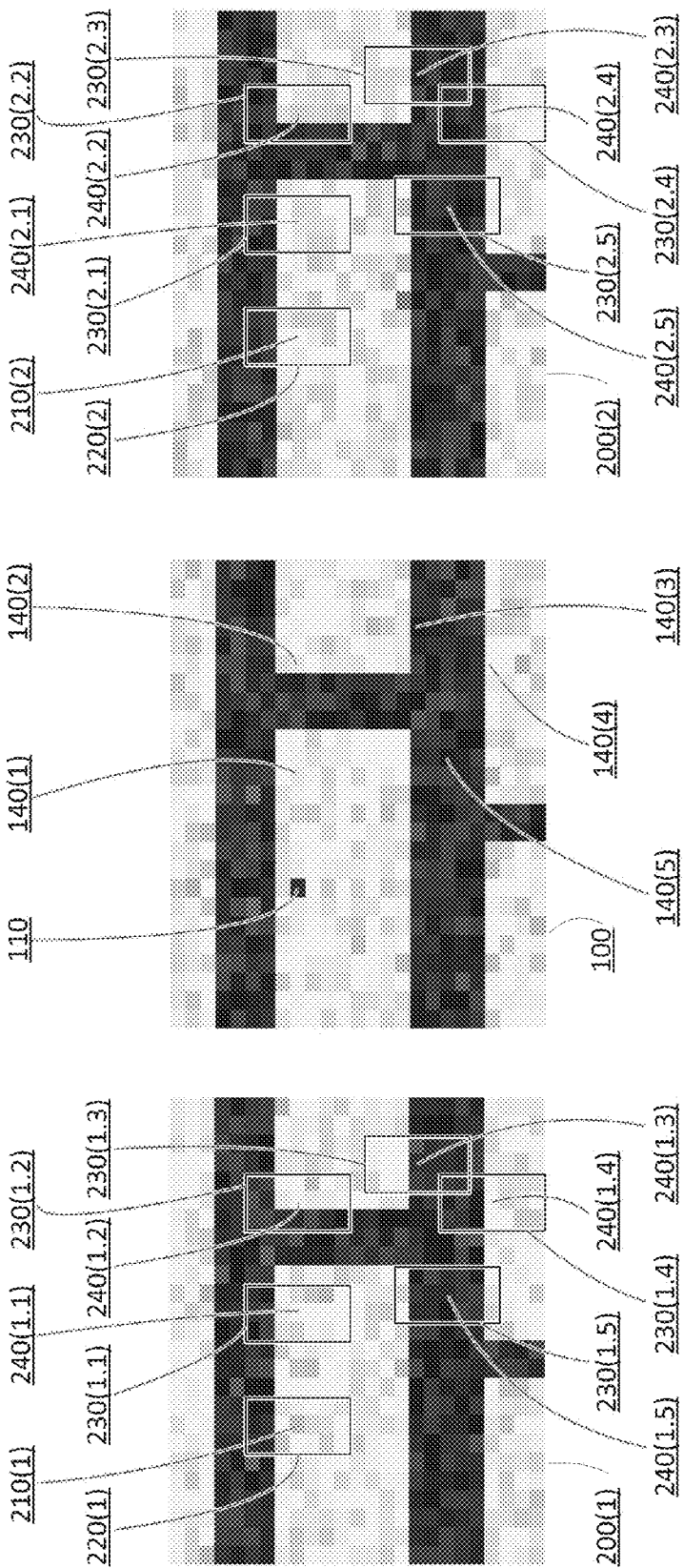
FIG. 9 illustrates an inspection image and multiple reference images, according to an embodiment of the invention.

FIG. 9 illustrates inspection image 100 and multiple reference images, images 200(1) and 200(2), according to an embodiment of the invention. In the illustrated example, the source and reference patches defined in each of the reference images are of the same shape, but this is not necessarily so. It is noted that method 700 is not limited to utilization of only two reference images, and more images may also be used.

Reverting to FIG. 8, stage 720 includes: in each out of multiple reference images defining a source patch associated with a reference source pixel of that reference image, wherein the reference source pixel corresponds to the candidate pixel. Referring to the example of FIG. 9, it is noted that the multiple reference images may include reference images 200(1) and 200(2), and that the corresponding source patches may be patch 220(1) (which is associated with source pixel 210(1) of reference image 200(1)) and patch 220(2) (which is associated with source pixel 210(2) of reference image 200(2)). As discussed in more detail with respect to method 800, optionally stage 720 may include defining more than one source patch in one of these reference images (or in some of them). That is, stage 720 may include multiple instances of stage 620.

Optional stage 730 includes defining in each of the reference images multiple reference patches. Stage 730, if implemented, includes multiple instances of stage 530 and/or 630, for each of the reference images of stage 720.

Stage 740 includes determining in each of the reference images a similarity level with respect to each of a plurality of reference patches included in that reference image, based on the source patch (or respective source patch, if more than one is defined in this reference image) and on a predefined patch-similarity criterion. A single patch-similarity criterion may be used in all reference images; alternatively different criterions may be used in different reference images. For example, the similarity criterion may be based on image parameters such as average gray level, image noise level, etc. Stage 740 includes multiple instances of stage 540 and/or 640.

Stage 750 includes rating each out of multiple inspected pixels with a representative score which is based on similarity levels of references patches of different reference images. Each of these reference patches is associated with a reference pixel of the respective reference image which corresponds to the inspected pixel. Referring to stage 550, it is noted that stage 750 may be regarded as an implementation of stage 550 in which at least one of the representative scores with which one of the multiple inspected pixels is rated is based also on at least one Nth similarity level of a reference patch associated with a reference pixel of an Nth reference image which corresponds to the inspected pixel (N≥2). Referring to the examples set forth with respect to the previous drawings, stage 750 may be carried out by an evaluation module such as evaluation module 940.

The representative scores which are determined in stage 750 may later be used in some or all of stages 760, 770, 780, and 790, which are similar to stages 560, 570, 580, and 590 (respectively). For reasons of brevity of disclosure, the discussion which relates to stages 560, 570, 580, and 590 is not repeated here, because it applies to method 700 as well. It would be clear to a person who is of skill in the art that stage 760 includes selecting pixels of the inspection image based on multiple representative scores of pixels of the inspection image, and that stage 770 includes determining a presence of a defect in the candidate pixel based on the inspected values of these selected inspected pixels—which, as aforementioned, were selected based on similarity levels which pertain to source patches of different reference images.

Stage 740 includes determining with respect to each out of a plurality of pixels of the inspection image a plurality of similarity levels (each relating to a reference patch of a different reference image, a patch which is associated with a pixel of that reference image which corresponds to the relevant pixel of the inspection image).

Utilizing source patches of different reference images may be implemented for various reasons, such as providing a better statistical reference (e.g. if multiple reference images are used for the comparison of the candidate pixel to other pixels), requiring stricter standard of similarity, etc. The rating of pixels of the inspection image may account in various ways for different similarity standards.

For example, the rating of stage 750 may be implemented so that at least one representative score is determined based on a group of similarity levels of reference patches from multiple reference images, so that the score indicates a low degree of similarity between an environment of the inspected pixel and an environment of the candidate pixel if any of the respective similarity levels indicates a low degree of similarity—even if corresponding similarity levels from other reference images indicate a higher level of similarity.

For example, assuming that the similarity levels for all patches are given as a score between 1 and 100 (or any other range shared between all of them), then a score which is determined as the minimum of these similarity levels (Score=Min[SL1 . . . SLN]). In such cases, it is clear that even if only one of the similarity levels SL1 . . . SLN is low, the computed score will be equal to this similarity level, and therefore also be low.

It is noted that more generally, if N≥2 similarity levels are determined for multiple reference patches which are associated with pixels which correspond to a given inspection image pixel, then the representative score may be determined (i.e. based on rules, criterions, etc., which necessitate the following) so that it would indicate a low degree of similarity between an environment of the respective inspected pixel and an environment of the candidate pixel if at least M (1≤M<N) of the respective similarity levels indicate low degrees of similarity. This may be implemented, for example, by averaging the M lowest levels, by basing the computation on the Mth lowest level, etc.

Referring to an implementation of method 700 (also of method 500) in which patches are determined and utilized in two reference images (e.g. as exemplified in FIG. 9), it is noted that such a method includes: based on a second source patch defined in a second reference image (and on a respective patch-similarity criterion), determining a similarity level with respect to each of a plurality of reference patches, each of which is associated with a pixel of the second reference image. Furthermore, at least one of the representative scores with which one of the multiple inspected pixels is rated is based also on a similarity level of a reference patch associated with a reference pixel of the second reference image which corresponds to the inspected pixel.

FIG. 10 is a flowchart of computerized method 800 for inspecting an article for defects based on processing of inspection images generated by collecting signals arriving from the article, according to an embodiment of the invention.

Method 800 is a variation of method 500, in which patches of different shapes are implemented in each out of multiple reference images. The numbering of the stages of method 800 is similar to that of method 500 (e.g. stage 820 is equivalent to stage 520). All variations and possible implementations which are discussed with respect to a given stage of method 500 may be implemented, mutatis mutandis, for the equivalent stage of method 800.

Method 800 may be regarded as a combination of methods 500, 600, and 700. Stages 520, 530, and 540 are repeated for each of a plurality of reference images (wherein for at least one of, possibly a plurality of, and even all of the reference images, stage 620, 630 and 640 are executed). The rating of stage 850 is based on the similarity levels determined for patches of multiple reference images and of different shapes. In the following discussion only reference images for which patches of multiple shapes are defined, are mentioned. However, as mentioned above, in some of these reference images only one source patch is used.

Stage 820 may include defining in each out of multiple reference images multiple source patches of different shapes, wherein each of the multiple source patches is associated with the reference source pixel of the respective reference image.

Stage 830 may include defining in each of the reference images multiple reference patches for each of the source patches of that reference image.

Stage 840 may include: In each of the reference images: for each of the multiple source patches, determining based on that source patch and on a respective patch-similarity criterion (i.e. respective to the source patch), multiple similarity levels. Each of these similarity levels is defined with respect to one of a respective plurality of reference patches (which are related to one source patch), which is associated with a reference image pixel.

Stage 850 may include rating each out of the multiple inspected pixels with a representative score which is based on the plurality of similarity levels determined with respect to multiple reference patches associated with each out of a plurality of pixels of the multiple reference images which corresponds to that inspected pixel.

Optionally, stage 845 in which intermediates scores are computed may be executed for computing with respect to each inspected pixel out of the multiple inspected pixels multiple intermediate scores, each of which is computed based on the plurality of similarity levels determined for a corresponding reference image pixel of one of the reference images.

It is noted that for each of the multiple inspected pixels which is rated with a representative score, the representative score may be based on one of the following:

One similarity level, determined with respect to the reference patch which is associated with the pixel which corresponds to that inspected pixel in one of the reference images;

A plurality of similarity levels determined with respect to multiple reference patches which are associated with a pixel which corresponds to that inspected pixel in one of the reference images.

A plurality of similarity levels determined with respect to multiple reference patches associated with each out of a plurality of pixels of multiple reference images which corresponds to that inspected pixel.

A combination of two or more of the above (with respect to different reference images).

By way of example, if K similarity levels are determined with respect to patches associated with a pixel which correspond to a inspected pixel in each out of Q reference images, the representative score for that inspected image pixel may be regarded as f(p1,1 ... p1,k, ..., pq,1 ... pq,k), wherein pi, j is the similarity level determined with respect to the pixel which corresponds to the candidate pixel in the ith reference image, based on the jth kernel.

The function f may be a sum of multiple functions which are applied to subgroups of the similarity levels. For example, f may be equal to $\Sigma_1{}^q fi(pi,1 \ldots pi,k)$.

$$\Sigma_1{}^q fi(p_{i,1}, \ldots p_{i,k}) fi(p_{i,1} \ldots p_{i,k})$$

The function f, or any one of the sub-functions whose sum is equal to f, may be a linear function, a polynomial function, a logarithmic function, an absolute-value function, a maximum or minimum value function, or any combination of the above, and may be any other function. The selection of the exact function depends on various factors such as the kinds of defects which are looked for, the noise level of the environment, and so on.

Referring to method 500 as well as to method 800, it is noted that optionally such methods may include executing in each image out a plurality of images which includes the reference image: (a) defining multiple source patches of different shapes, wherein each of the multiple source patches is associated with a reference source pixel of the image; and (b) for each of the source patches of the image: based on the source patch and a respective patch-similarity criterion, determining a similarity level with respect to each of a plurality of reference patches, each of which is associated with a pixel of the image; thereby for each of a plurality of pixels of the image, determining a plurality of similarity levels that are determined for multiple reference patches of different shapes which are associated with the respective pixel of the image. Following this, the stage of rating may include rating each inspected pixel out of at least one of the multiple inspected pixels with a representative score which is based on multiple similarity levels of reference patches associated with pixels of the plurality of images which correspond to the inspected pixel.

Such methods may include computing a score (which may be the representative score, or an intermediate score) with respect to each inspected pixel out of the subgroup which includes at least one of the multiple inspected pixels, based on the plurality of similarity levels determined for the corresponding pixels of the plurality of images, so that the score indicates a high degree of similarity between an environment of the inspected pixel and an environment of the candidate pixel if for all of the corresponding pixels of the plurality of images, at least one of the respective similarity levels indicates a high degree of similarity; wherein the selecting of the multiple selected inspected pixels is based on results of the computing.

The determining of the presence of the defect in the candidate pixels in any of the aforementioned methods (in stages 570, 670, 770 and 870) may be implemented in various ways. As noted above, such determining is based on the inspected value of the candidate pixel and on the inspected values of the selected inspected pixels. It is noted that such determining may be further based on patches surrounding those pixels, e.g. similarly to the discussion of the determining of the similarity levels. Variations discussed below may be implemented, mutatis mutandis, also for determination of the presence of the defect based on patches larger than a single pixel.

Optionally, such a determining may include setting a threshold, based on the inspected values of the selected pixels (with or without additional parameters), and comparing the inspected value of the candidate pixel to the set threshold. For example, if the inspected value of the candidate pixel is higher (or, alternatively, lower) than the set threshold then the determining of the presence of the defect includes determining that there is a defect in the candidate pixel, but if it is lower (or, alternatively, higher) than that threshold then it would be determined that there is no defect in the candidate pixel.

If the inspected value of each of these pixels (the candidate pixel and the selected pixel) is a gray level, the determining of the presence of the defect may be based on a grey level value of the candidate pixel and on a threshold determined which is based on grey level values of the selected inspected pixels.

It is noted that more than one threshold may be determined based on the inspected values of the selected pixel. For example, two thresholds may be set, thereby defining a range of inspected values so that if the inspected value of the candidate pixel is outside that range, the determining of the presence of defects includes determining that there is a defect in the candidate pixel, but if it is within that range then it would be determined that there is no defect in the candidate pixel.

For example, the inspected value of the candidate pixel may be compared to the inspected value of the selected pixel having the highest (or lowest) inspected value out of the group of selected pixels. If the difference between those values exceeds a threshold (which may be determined based on the inspected values, but not necessarily so), then the candidate pixel may be considered as defective.

In another example, the ratio between: (a) the difference between the inspected value of the candidate pixel and the average of inspected values of all selected pixel; and (b) the difference between the inspected value of the selected pixel having the highest (or lowest) inspected value and the average inspected value of the group of selected pixels is determined. This ratio may be compared to a threshold (which may be determined based on the inspected values, but not necessarily so), and the classification of the candidate pixel as defective or not may be based on that comparison. Other ways of comparing the inspected value of the candidate pixel and those of the selected pixel may clearly also be implemented in other implementations, and only few examples have been provided.

It is noted that different types of averages may be implemented, e.g. arithmetic mean, median, geometric median, geometric mean, harmonic mean, quadratic mean, weighted mean, truncated mean, interquartile mean, midrange, winsorized mean, and so forth.

Figure 11:
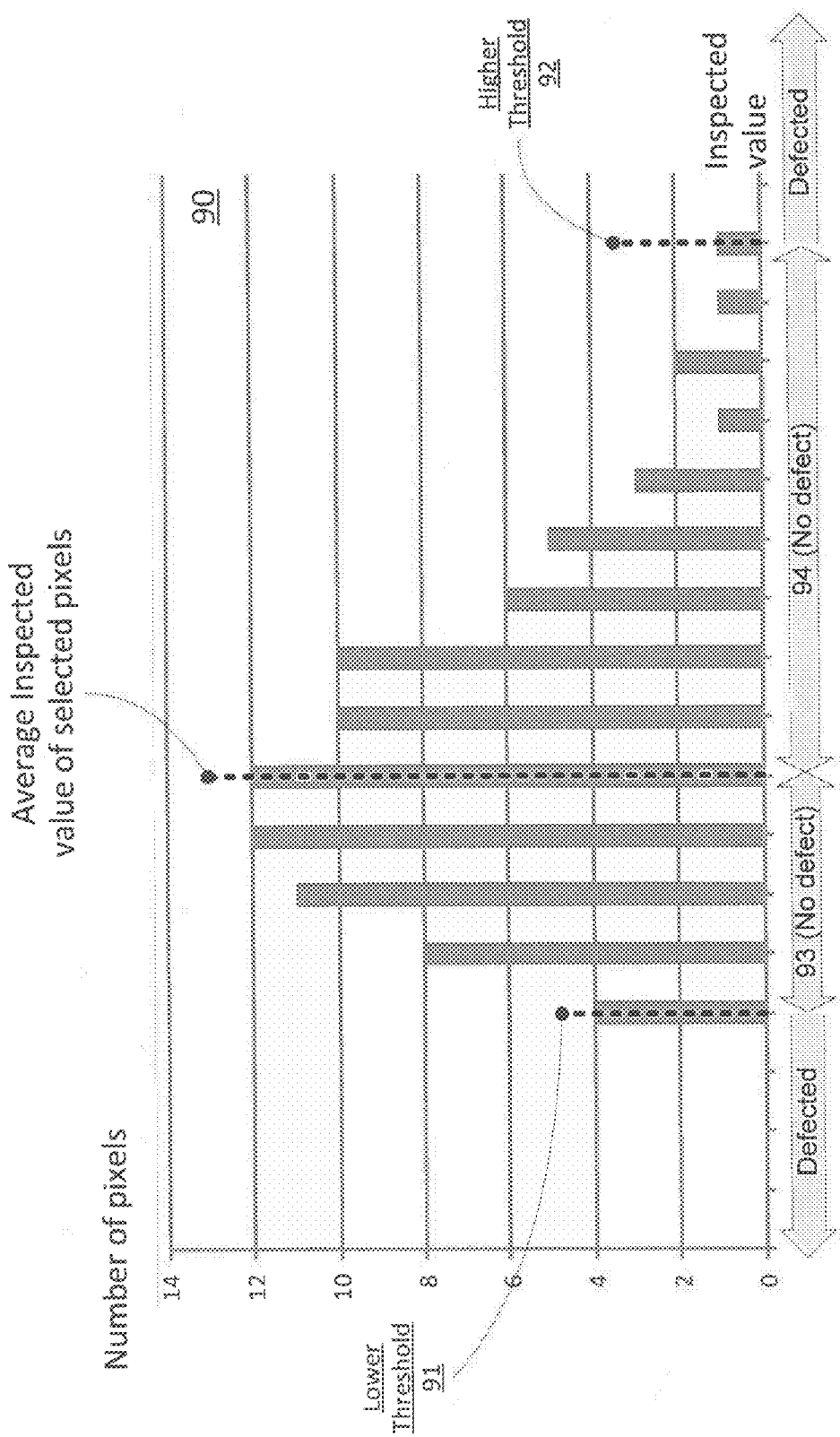
FIG. 11 is an example of a possible distribution of the inspected values of the selected inspected pixel.

Optionally, the determining of the presence of the defect may be based on the inspected value of the candidate pixel, on an average of the inspected values of the selected inspected pixels, and on asymmetric decision rules which are asymmetric with respect to an equality of the average and the inspected value of the candidate pixel. FIG. 11 is an example of a possible distribution of the inspected values (e.g. GL values) of the selected inspected pixel. The abscissa represents the inspected values and the ordinate represents the number of selected pixels having each of the inspected values.

As can be seen, in the example of FIG. 11 the group of inspected values which includes all of the inspected values of the selected inspected pixels includes fourteen discrete inspected values, of which only four are lower than the average, and nine are larger than the average. In an example of asymmetric decision rules, two thresholds 91 and 92 may be set. Lower threshold 91 is met if the inspected value of the candidate pixel is four levels below the average level, and higher threshold 92 is met if the inspected value of the candidate pixel is nine levels above the average level (nine being different than four in the provided example suggests that the rules are asymmetric). As can be seen, the difference 93 between the equality point and the lower threshold 91 is smaller than the difference 94 between the equality point and the higher threshold 92.

A possible generalized example of asymmetric decision rules is that the determining of the presence of the defect includes determining that there is a defect in the candidate pixel if and only if either (a) the inspected value of the candidate pixel is larger than the average inspected value of the group of selected pixels by at least X or (b) the inspected value of the candidate pixel is smaller than the average inspected value of the group of selected pixels by at least Y, wherein X is different than Y.

It will also be understood that any of methods 500, 600, 700 and 800 may be implemented by a system which is a suitably programmed computer. Likewise, a computer program may be implemented, being readable by a computer for executing any of one or more out of methods 500, 600, 700 and 800. A machine-readable memory may be implemented, tangibly embodying a program of instructions executable by the machine for executing any of one or more out of methods 500, 600, 700 and 800.

Figure 12:
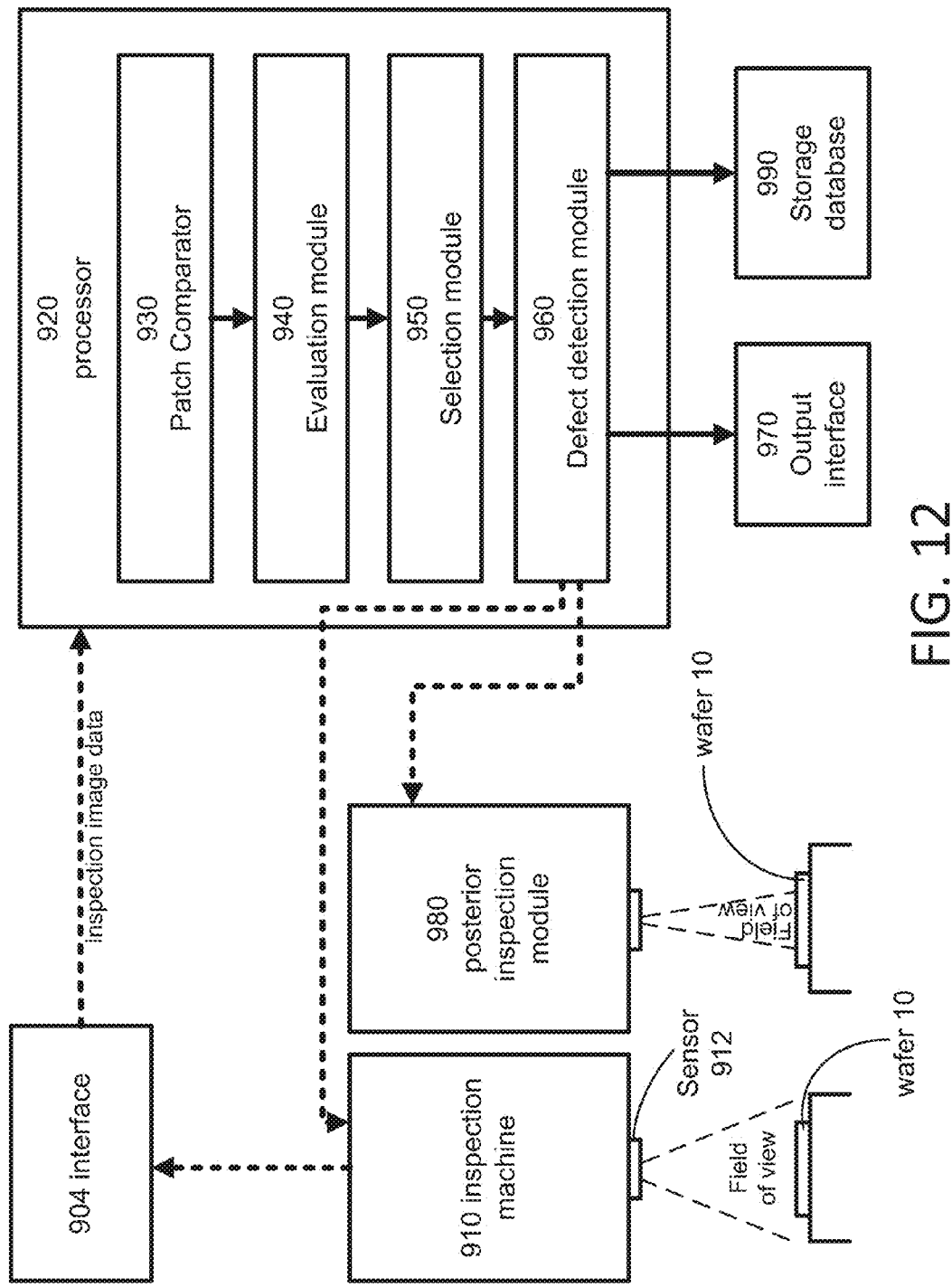
FIG. 12 is a block diagram of a system which is capable of inspecting an article for defects, according to an embodiment of the invention.

FIG. 12 is a block diagram of system 900 which is capable of inspecting an article for defects, according to an embodiment of the invention. While not necessarily so, the article may be selected from a group consisting of an electronic circuit, a wafer, and a photomask.

System 900 inspects such articles for defects based on processing of inspection images generated by collecting signals arriving from the article. The processed images include at least one inspection image (such as inspection image 100) and at least one reference image (such as reference image 200). System 900 may obtain the inspection images in many ways. For example, system 900 may be combined with an inspection machine 910 that is used to inspect the wafer (e.g. during different stages of manufacturing thereof). In another implementation, system 900 may be connected to such an inspection machine, or the inspection image may be transmitted by an off-line device connected to only one of the machines at a time. Also, system 900 may be an inspection machine into which some or all of the modifications and/or features discussed below have been integrated.

The inspection machine/unit which is used for collecting the signals from the article can be implemented by various detection tools, as means, methods and systems for obtaining pixels are known in the art. The detection tools may have a single detector, multiple detectors, dark field detectors, bright field detectors or any combination of detectors.

As will be discussed below in more detail, one or more of the components of system 900 may be used to classify potential defects that were detected in an inspected image of the wafer. This determined classification may later be used in manufacturing of the wafer, and/or in later stages of inspection of the wafer.

While not necessarily so, the process of operation of system 900 may correspond to some or all of the stages of any one of methods 500, 600, 700 and 800. Likewise, methods 500, 600, 700 and 800 and their possible implementations may possibly be implemented by a system such as system 900. It is therefore noted that embodiments of the invention discussed in relation to any one of methods 500, 600, 700 and 800 may also be implemented, mutatis mutandis, in a hardware counterpart as various embodiments of system 900, and vice versa.

It should be noted that, as will be clear to any person who is of skill in the art, wherever the term "wafer" is used—similar techniques, systems, methods and computer program products may be implemented for optical masks that are used for the manufacturing of wafers.

Without limiting the scope of the invention in any way, in some possible implementations system 900 may be used for inspection tools in which an entire wafer or at least an entire die is scanned for detection of potential defects (such as the Elite and the UVision systems by Applied Materials, Inc.), and/or for review tools which are typically of higher resolution (e.g. a scanning electron microscope, SEM) which are used for ascertaining whether a potential defect is indeed a defect. Such review tools usually inspect fragments of a die, one at a time, in high resolution. Whenever the term "inspection" or its derivatives are used in this disclosure, such an inspection is not limited with respect to resolution or size of inspection area, and may be applied, by way of example, to review tools and to lower resolution wafer inspection tools alike.

The scanning of the wafer 10 may be implemented by any scanning, imaging and/or detecting apparatus, many of which are known in the art. Such an apparatus (denoted "sensor 912") may be part of system 900, but this is not necessarily so and the two may or may not be directly connected. By way of example, such an apparatus may be a scanning electron microscope, an optical inspection system and so forth. Wafer 10 may be similar to prior art wafer 10 discussed in the Background.

By way of example, a wafer 10 (or several wafers) may be placed on a movable stage. In such an implementation, wafer 10 may remain stationary with respect to the movable stage during the scanning of wafer 10, and the respective movement between wafer 10 and sensor 912 (if required to image different parts of the wafer) is achieved by controllably moving the movable stage. For example, the movable stage may be moved along an X-axis, a Y-axis, and possibly also a Z-axis direction (wherein the X and Y axes are perpendicular axes on the surface plane of the movable stage, and the Z-axis is perpendicular to both of those axes). Alternatively (or in addition), sensor 912 may change a position in order to image different parts of wafer 10.

System 900 includes one or more processors 920 which are capable of inspecting articles for defects (in FIG. 12 only one processor is illustrated, for sake of simplicity of the illustration).

System 200 further includes modules 930, 940, 950 and 960 which are capable of processing data, as discussed below. These modules (which may be implemented independently from one another, but not necessarily so) may be implemented by any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof. Each of modules 930, 940, 950 and 960 can be made up of any combination of software, hardware and/or firmware that performs the functions as defined and explained herein. The modules in the figures may be centralized in one location or dispersed over more than one location.

Patch comparator 930 is capable of comparing different patches, and to determine similarity levels indicative of the similarity between different patches. Optionally, patch comparator 930 may compare a patch selected from a given image (e.g. reference image 200) only to other patches of the same image.

Patch comparator 930 is configured to determine with respect to each of a plurality of reference patches in a reference image a similarity level, based on a predefined patch-similarity criterion and on a source patch which is defined in the reference image and which is associated with a reference source pixel of the reference image. The reference source pixel corresponds to a candidate pixel of an inspection image that is generated by collecting signals arriving from the article. Similarly to the methods discussed above, the candidate pixel is representative of a candidate article defect location. Each of the plurality of reference patches is associated with a reference image pixel.

Examples of ways in which patch comparator 930 may operate are discussed in further detail in relation to aforementioned stages 540, 640, 740 and 840.

It is noted that optionally, the source patch and/or the multiple reference patch in any of the one or more reference images 200 may be defined by patch comparator 230.

Optionally, patch comparator 930 may be configured to define in the reference image the source patch (associated with a reference source pixel of the reference image, which corresponds to the candidate pixel of the inspection image). Optionally, patch comparator 930 may be configured to define in the reference image multiple reference patches (e.g. based on information of the source patch). Alternatively, other modules (either parts of system 900 or others) may execute these patch defining processes. Patch comparator 930 is also referred to as a "Kernel comparison module".

Evaluation module 940 is capable of rating pixels of the inspection image 100, based on the similarity levels determined with respect to patches of one or more reference images 200. Evaluation module 940 is configured to rate each inspected pixel out of multiple inspected pixels of the inspection image with a representative score which is based on the similarity level of a reference patch associated with a reference pixel corresponding to the inspected pixel. Examples of ways in which evaluation module 940 may operate are discussed in further detail in relation to aforementioned stages 550, 650, 750 and 850. It is noted that modules 930 and 940 may be implemented as a single module.

Selection module 950 is configured to select multiple selected inspected pixels based on the representative scores of the multiple inspected pixels. Examples of ways in which selection module 950 may operate are discussed in further detail in relation to aforementioned stages 560, 660, 760 and 860.

Defect detection module 960 is capable of using information of the selected pixels (optionally only of the selected pixels and of the candidate pixel) for determining a presence of a defect in the candidate pixel. Defect detection module 960 is configured to determine a presence of a defect in the candidate pixel based on an inspected value of the candidate pixel and inspected values of the selected inspected pixels. Examples of ways in which defect detection module 960 may operate are discussed in further detail in relation to aforementioned stages 570, 670, 770 and 870. It is noted that module 960 may also be regarded as a classification module, as it may classify pixels into classes (e.g. "defective"/"non-defective").

Optionally, defect detection module 960 may be configured to determine the presence of the defect based on a grey level value of the candidate pixel and on a threshold determined based on grey level values of the selected inspected pixels (as discussed in more detail with respect to methods 500, 600, 700 and 800 and to FIG. 11).

Optionally, defect detection module 960 may be configured to determine the presence of the defect based on the inspected value of the candidate pixel, on an average of the inspected values of the selected inspected pixels, and on asymmetric decision rules which are asymmetric with respect to an equality of the average and the inspected value of the candidate pixel.

As discussed with respect to the aforementioned methods, the patches may be relatively small. For example, a size of a smallest rectangle in which all pixels of the source patch are enclosed is smaller than 0.05 times a size of the inspection image.

It is noted that system 900 may implement different source patches of different shapes in the reference image. Multiple source patches of different shapes may be defined in the reference image (each of the multiple source patches is associated with the reference source pixel), and patch comparator 930 may be configured to determine for each of the multiple source patches, based on that source patch and a respective patch-similarity criterion, a similarity level with respect to each of a respective plurality of reference patches (each of which is associated with a reference image pixel). This way, for each of a plurality of reference image pixels, patch comparator 930 determines a plurality of similarity levels that are determined for multiple reference patches of different shapes which are associated with the respective reference image pixel. Accordingly, elevation module 940 may be configured to rate each inspected pixel out of a subgroup of the multiple inspected pixels with a representative score which is based on the plurality of similarity levels of the multiple reference patches which are associated with a reference pixel corresponding to the inspected pixel.

When utilizing patches of different shapes in a single reference image, evaluation module 940 may be configured to compute with respect to each inspected pixel out of the subgroup of inspected pixels a score, based on the plurality of similarity levels determined for the corresponding reference image pixel, so that the score indicates a high degree of similarity between an environment of the inspected pixel and an environment of the candidate pixel if any of the respective similarity levels indicates a high degree of similarity, wherein the selecting of the multiple selected inspected pixels is based on results of the computing.

System 900 may also be capable of determining a presence of a defect in the candidate pixel of the inspection image based on processing of patches in multiple reference images. Optionally, patch comparator 930 may be further configured to determine, based on a second source patch defined in a second reference image (and on a patch-similarity criterion which may be the same as the one used in the first reference image, but not necessarily so), a similarity level with respect to each of a plurality of reference patches, each of which is associated with a pixel of the second reference image. Evaluation module 940 may accordingly be configured to determine at least one of the representative scores with which one of the multiple inspected pixels is rated based also on a similarity level of a reference patch associated with a reference pixel of the second reference image which corresponds to the inspected pixel.

It is noted that more than two reference images may be used, and that patch comparator 930 may optionally be configured to determine, based on a source patch defined in each out of multiple reference images a similarity level with respect to each of a plurality of reference patches in that image. Evaluation module 940 may accordingly be configured to determine at least one of the representative scores with which one of the multiple inspected pixels is rated based on a similarity levels of reference patches associated with pixels of the multiple reference image which correspond to the inspected pixel.

Optionally, evaluation module 940 may be configured to determine the at least one representative score based on a group of similarity levels of reference patches from multiple reference images, so that the score indicates a low degree of similarity between an environment of the inspected pixel and an environment of the candidate pixel if any of the respective similarity levels indicates a low degree of similarity.

System 900 may also be capable of determining a presence of a defect in the candidate pixel by utilizing multiple patches of different shapes in each out of multiple reference images. Optionally, in each image out a plurality of images which includes the reference image multiple source patches of different shapes are defined, each of the multiple source patches is associated with a reference source pixel of the image.

Patch comparator 930 may be configured to determine in each image of the plurality of images, for each of the source patches of the image a similarity level with respect to each of a plurality of reference patches based on the source patch and a respective patch-similarity criterion (each of the plurality of reference patches being associated with a pixel of the image). Thereby, for each of a plurality of pixels of the image, patch comparator 930 determines a plurality of similarity levels that are determined for multiple reference patches of different shapes which are associated with the respective pixel of the image.

Evaluation module may accordingly be configured to rate each inspected pixel out of at least one of the multiple inspected pixels with a representative score which is based on multiple similarity levels of reference patches associated with pixels of the plurality of images which correspond to the inspected pixel.

Evaluation module 940 may be configured to compute with respect to each inspected pixel out of the at least one of the multiple inspected pixels a score, based on the plurality of similarity levels determined for the corresponding pixels of the plurality of images, so that the score indicates a high degree of similarity between an environment of the inspected pixel and an environment of the candidate pixel if for all of the corresponding pixels of the plurality of images, at least one of the respective similarity levels indicates a high degree of similarity. The selecting of the multiple selected inspected pixels in such a case is based on results of the computing.

As discussed with respect to the aforementioned methods, optionally selection module 950 may be configured to select in the inspection image a predetermined number of inspected pixels.

System 900 may include an optional communication interface (e.g. a cable, a wireless communication system, a computer, etc.) over which the images (the inspection image and the one or more reference images) are transferred from the inspection machine 910 to the corresponding processing modules.

System 900 may include an optional communication interface (e.g. a cable, a wireless communication system, a computer, etc.) which is configured for acquiring a list of at least one candidate pixel of the inspection image. Alternatively, an image processing module may be implemented (e.g. as part of processor 920), which is capable of processing the inspection image (and possibly also one or more reference images) for determining the list of at least one candidate pixel.

System 900 may include a tangible storage 990 (e.g. a hard-drive disk, a flash drive, etc.) for storing the results of the defect detection (e.g. a list of one or more defected pixels, if multiple candidate pixels are analyzed, or part thereof—e.g. only the defects which were classified as noteworthy) to a tangible storage. System 900 may also include an output interface 970 for transmitting the classification (or part thereof) to an external system (e.g. over cable connection or over wireless connection), wherein that external system may, in turn, act, based on the classification.

System 900 may also include an inspection module, which may be the aforementioned inspection machine 910 which provides the aforementioned inspection image by scanning of the inspected objects such as the wafers, and may alternatively be posterior inspection module 980 that is configured to inspect the wafer (or other inspected object) in higher resolution than that of the inspection image. This inspection module is configured to selectively scan, in a resolution higher than the resolution of the inspection image, areas of the inspected object which are selected based on the locations of identified items (e.g. potential defects) which are classified into certain classes but not into at least one of the other classes (i.e. refraining from selecting potential defects classified into at least one class other than the certain classes). The field of view of posterior inspection module 980 may be narrower than that of inspection machine 910, but this is not necessarily so.

In such a case, the areas selected for further scanning may be selected based on the locations of potential defects which are classified into certain classes but not into at least one of the other classes. For example, the scanning in the higher resolution may be carried out around the locations of the possible defects classified as "short gate", but not around the locations of the possible defects classified as "edge roughness".

It should be noted that inspection machine 910 and/or posterior inspection module 980, if implemented, may be implemented as inspection machines of various types, such as optical imaging machines, electron beam inspection machines, radars, LIDARs and so on.

Generally, identifying defects in a wafer (or in another inspected object) may be implemented using different techniques, among which are optical inspection and electron beam inspection. Utilization of system 900 may facilitate the use of more than a single inspection technique. For example, an initial inspection of the wafer is firstly carried out relatively quickly and in a coarse manner by inspection system 900 (e.g. using an optical inspection or an electron beam inspection set for coarse and fast inspection). Later, some of the potential defects found in the initial inspection (selected based on the classification results of classifier 950) are then studied again using a relatively slower but more exact inspection. Such posterior scanning may be executed either in another mode of inspection machine 910, or in a different posterior inspection module 980 (in a process also referred to as "reviewing", e.g. by DRSEM—Defect Review Scanning Electron Microscope).

System 900 may be implemented on a computer (such as a PC), e.g. the computer which implements the overall classification (Image Based Attributing, IBA) of the runtime inspection results, but this is not necessarily so. Each of the modules or components of system 900 may be implemented in software, hardware, firmware, or any combination thereof. Additionally, system 900 may also include other components that are not illustrated, and whose inclusion will be apparent to a person who is of skill in the art—e.g. a power source, a display, etc.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed is:

1. A computerized method for inspecting an article for defects based on processing of inspection images generated by collecting signals arriving from the article, the method comprising:
   obtaining a candidate pixel of the inspection image, the candidate pixel being representative of a candidate article defect location;
   in a reference image, defining a source patch associated with a reference source pixel of the reference image which corresponds to the candidate pixel;
   in the reference image, based on the source patch and a predefined patch-similarity criterion, determining a similarity level with respect to each of a plurality of reference patches, each of which is associated with a reference image pixel;
   in the inspection image, rating each inspected pixel out of multiple inspected pixels with a representative score which is based on the similarity level of a reference patch associated with a reference pixel corresponding to the inspected pixel;
   in the inspection image, selecting multiple selected inspected pixels based on the representative scores of the multiple inspected pixels;
   determining a presence of a defect in the candidate pixel based on an inspected value of the candidate pixel and inspected values of the selected inspected pixels; and
   in each image of a plurality of images which includes the reference image:
   (a) defining multiple source patches of different shapes, wherein each of the multiple source patches is associated with a reference source pixel of the image; and
   (b) for each of the source patches of the image: based on the source patch and a respective patch-similarity criterion, determining a similarity level with respect to each of a plurality of reference patches, each of which is associated with a pixel of the image;
   thereby for each of a plurality of pixels of the image, determining a plurality of similarity levels that are determined for multiple reference patches of different shapes which are associated with the respective pixel of the image;
   wherein the rating comprises rating each inspected pixel out of at least one of the multiple inspected pixels with a representative score which is based on multiple similarity levels of reference patches associated with pixels of the plurality of images which correspond to the inspected pixel.

2. The method according to claim 1, wherein the defining of the source patch comprises defining the source patch so that a size of a smallest rectangle in which all pixels of the source patch are enclosed is smaller than 0.05 times a size of the inspection image.

3. The method according to claim 1, wherein the determining of the presence of the defect is based on a grey level value of the candidate pixel and on a threshold determined based on grey level values of the selected inspected pixels.

4. The method according to claim 1, comprising:
defining in the reference image multiple source patches of different shapes, wherein each of the multiple source patches is associated with the reference source pixel; and
for each of the multiple source patches, based on that source patch and a respective patch-similarity criterion, determining a similarity level with respect to each of a respective plurality of reference patches, each of which is associated with a reference image pixel; thereby for each of a plurality of reference image pixels, determining a plurality of similarity levels that are determined for multiple reference patches, of different shapes, which are associated with the respective reference image pixel;
wherein the rating of each inspected pixel out of multiple inspected pixels comprises rating each inspected pixel out of a subgroup of the multiple inspected pixels with a representative score which is based on the plurality of similarity levels of the multiple reference patches which are associated with a reference pixel corresponding to the inspected pixel.

5. The method according to claim 1, further comprising:
defining a plurality of reference patches in a second reference image;
based on a second source patch defined in the second reference image, determining a similarity level with respect to each of the plurality of reference patches in the second reference image to the second source patch, each of plurality of reference patches in the second reference image being associated with a pixel of the second reference image;
wherein at least one of the representative scores with which one of the multiple inspected pixels is rated is based also on a similarity level of a reference patch associated with a reference pixel of the second reference image which corresponds to the inspected pixel.

6. The method according to claim 5, wherein the at least one representative score is determined based on a group of similarity levels of reference patches from multiple reference images, so that the score indicates a low degree of similarity between an environment of the inspected pixel and an environment of the candidate pixel if any of the respective similarity levels indicates a low degree of similarity.

7. A system capable of inspecting an article for defects, the system comprising:
a memory; and
a processor electronic device operatively coupled to the memory, the processor electronic device to:
determine with respect to each of a plurality of reference patches in a reference image a similarity level, based on a predefined patch-similarity criterion and on a source patch which is defined in the reference image and which is associated with a reference source pixel of the reference image; wherein the reference source pixel corresponds to a candidate pixel of an inspection image that is generated by collecting signals arriving from the article, the candidate pixel being representative of a candidate article defect location; wherein each of the plurality of reference patches is associated with a reference image pixel;
rate each inspected pixel out of multiple inspected pixels of the inspection image with a representative score which is based on the similarity level of a reference patch associated with a reference pixel corresponding to the inspected pixel;
select multiple selected inspected pixels based on the representative scores of the multiple inspected pixels; and
determine a presence of a defect in the candidate pixel based on an inspected value of the candidate pixel and inspected values of the selected inspected pixels,
wherein in each image of a plurality of images, which includes the reference image, multiple source patches of different shapes are defined, each of the multiple source patches is associated with a reference source pixel of the image;
wherein to determine the similarity level comprises the processor electronic device to determine in each image of the plurality of images, for each of the source patches of the image a similarity level with respect to each of a plurality of reference patches based on the source patch and a respective patch-similarity criterion, wherein each of the plurality of reference patches is associated with a pixel of the image;
thereby for each of a plurality of pixels of the image, determining a plurality of similarity levels that are determined for multiple reference patches of different shapes which are associated with the respective pixel of the image;
wherein to rate each inspected pixel comprises the processor electronic device to rate each inspected pixel out of at least one of the multiple inspected pixels with a representative score which is based on multiple similarity levels of reference patches associated with pixels of the plurality of images which correspond to the inspected pixel.

8. The system according to claim 7, wherein a size of a smallest rectangle in which all pixels of the source patch are enclosed is smaller than 0.05 times a size of the inspection image.

9. The system according to claim 7, wherein the processor electronic device is further to determine the presence of the defect based on a grey level value of the candidate pixel and on a threshold determined based on grey level values of the selected inspected pixels.

10. The system according to claim 7, wherein multiple source patches of different shapes are defined in the reference image, each of the multiple source patches is associated with the reference source pixel;
wherein the processor electronic device is further to determine for each of the multiple source patches, based on that source patch and a respective patch-similarity criterion, a similarity level with respect to each of a respective plurality of reference patches, each of which is associated with a reference image pixel; thereby for each of a plurality of reference image pixels, determining a plurality of similarity levels that are determined for multiple reference patches of different shapes which are associated with the respective reference image pixel; and
rate each inspected pixel out of a subgroup of the multiple inspected pixels with a representative score which is based on the plurality of similarity levels of the multiple reference patches which are associated with a reference pixel corresponding to the inspected pixel.

11. The system according to claim 7, wherein the processor electronic device is further to:
define a plurality of reference patches in a second reference image;
determine, based on a second source patch defined in the second reference image, a similarity level with respect to each of plurality of reference patches in the second reference image to the second source patch, each of plurality of reference patches in the second reference image being associated with a pixel of the second reference image; and determine at least one of the representative scores with which one of the multiple inspected pixels is rated based also on a similarity level of a reference patch associated with a reference pixel of the second reference image which corresponds to the inspected pixel.

12. The system according to claim 11, wherein the processor electronic device is further to determine the at least one representative score based on a group of similarity levels of reference patches from multiple reference images, so that the score indicates a low degree of similarity between an environment of the inspected pixel and an environment of the candidate pixel if any of the respective similarity levels indicates a low degree of similarity.

13. A program storage device readable by machine, tangibly embodying a program of instructions executable by the machine to perform a method for inspecting an article for defects based on processing of inspection images generated by collecting signals arriving from the article, the method comprising:

obtaining a candidate pixel of the inspection image, the candidate pixel being representative of a candidate article defect location;

in a reference image, defining a source patch associated with a reference source pixel of the reference image which corresponds to the candidate pixel;

in the reference image, based on the source patch and a predefined patch-similarity criterion, determining a similarity level with respect to each of a plurality of reference patches, each of which is associated with a reference image pixel;

in the inspection image, rating each inspected pixel out of multiple inspected pixels with a representative score which is based on the similarity level of a reference patch associated with a reference pixel corresponding to the inspected pixel;

in the inspection image, selecting multiple selected inspected pixels based on the representative scores of the multiple inspected pixels;

determining a presence of a defect in the candidate pixel based on an inspected value of the candidate pixel and inspected values of the selected inspected pixels; and in each image of a plurality of images which includes the reference image:
(a) defining multiple source patches of different shapes, wherein each of the multiple source patches is associated with a reference source pixel of the image; and
(b) for each of the source patches of the image: based on the source patch and a respective patch-similarity criterion, determining a similarity level with respect to each of a plurality of reference patches, each of which is associated with a pixel of the image;

thereby for each of a plurality of pixels of the image, determining a plurality of similarity levels that are determined for multiple reference patches of different shapes which are associated with the respective pixel of the image;

wherein the rating includes rating each inspected pixel out of at least one of the multiple inspected pixels with a representative score which is based on multiple similarity levels of reference patches associated with pixels of the plurality of images which correspond to the inspected pixel.

14. The program storage device according to claim 13, wherein the defining of the source patch includes defining the source patch so that a size of a smallest rectangle in which all pixels of the source patch are enclosed is smaller than 0.05 times a size of the inspection image.

15. The program storage device according to claim 13, wherein the determining of the presence of the defect is based on a grey level value of the candidate pixel and on a threshold determined based on grey level values of the selected inspected pixels.

16. The program storage device according to claim 13, wherein the program of instructions further include instructions executable by the machine for: (a) defining in the reference image multiple source patches of different shapes, wherein each of the multiple source patches is associated with the reference source pixel; and (b) for each of the multiple source patches, based on that source patch and a respective patch-similarity criterion, determining a similarity level with respect to each of a respective plurality of reference patches, each of which is associated with a reference image pixel; thereby for each of a plurality of reference image pixels, determining a plurality of similarity levels that are determined for multiple reference patches, of different shapes, which are associated with the respective reference image pixel; wherein the rating includes rating each inspected pixel out of a subgroup of the multiple inspected pixels with a representative score which is based on the plurality of similarity levels of the multiple reference patches which are associated with a reference pixel corresponding to the inspected pixel.

17. The program storage device according to claim 13, wherein the program of instructions further include instructions executable by the machine for:

defining a plurality of reference patches in a second reference image;

based on a second source patch defined in the second reference image and optionally also on a second patch-similarity criterion, determining a similarity level with respect to each of the plurality of reference patches in the second reference image to the second source patch, each of plurality of reference patches in the second reference image being associated with a pixel of the second reference image;

wherein at least one of the representative scores with which one of the multiple inspected pixels is rated is based also on a similarity level of a reference patch associated with a reference pixel of the second reference image which corresponds to the inspected pixel.

* * * * *